(12) United States Patent
Nishiura et al.

(10) Patent No.: US 8,431,249 B2
(45) Date of Patent: Apr. 30, 2013

(54) DIBENZO[C,G]FLUORENE COMPOUND AND ORGANIC LIGHT-EMITTING DEVICE USING SAME

(75) Inventors: Chiaki Nishiura, Kawasaki (JP); Jun Kamatani, Tokyo (JP); Shigemoto Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 175 days.

(21) Appl. No.: 13/127,657

(22) PCT Filed: Oct. 29, 2009

(86) PCT No.: PCT/JP2009/068934
§ 371 (c)(1),
(2), (4) Date: May 4, 2011

(87) PCT Pub. No.: WO2010/053141
PCT Pub. Date: May 14, 2010

(65) Prior Publication Data
US 2011/0260150 A1    Oct. 27, 2011

(30) Foreign Application Priority Data
Nov. 6, 2008  (JP) ................. 2008-285377

(51) Int. Cl.
*B32B 9/00*  (2006.01)

(52) U.S. Cl.
USPC ...... 428/690; 428/917; 313/504; 252/301.16; 564/426; 548/128; 548/131; 548/262

(58) Field of Classification Search .......... 428/690, 428/917; 313/504; 252/301.16; 564/426; 548/128, 131, 262
See application file for complete search history.

(56) References Cited

U.S. PATENT DOCUMENTS
2004/0131880 A1   7/2004 Zheng et al.

FOREIGN PATENT DOCUMENTS
WO    WO 03/051092 A    6/2003

*Primary Examiner* — Shane Fang
(74) *Attorney, Agent, or Firm* — Canon U.S.A., Inc., IP Division

(57) ABSTRACT

An organic light-emitting device is provided which efficiently emits light with high brightness and has durability. The organic light-emitting device includes a dibenzo[c,g]fluorene compound having two dibenzo[c,g]fluorene skeletons, and has an organic compound layer containing the dibenzo[c,g]fluorene compound.

6 Claims, 1 Drawing Sheet

DIBENZO [a,h] FLUORENE

DIBENZO [a,i] FLUORENE

DIBENZO [c,g] FLUORENE

DIBENZO [a,h] FLUORENE   DIBENZO [a,i] FLUORENE   DIBENZO [c,g] FLUORENE

COMPOUND A    LUMO / HOMO

COMPOUND B    LUMO / HOMO

DIBENZO[C,G]FLUORENE COMPOUND AND ORGANIC LIGHT-EMITTING DEVICE USING SAME

TECHNICAL FIELD

The present invention relates to a dibenzo[c,g]fluorene compound and an organic light-emitting device using the same.

BACKGROUND ART

An organic light-emitting device is an electronic device in which a thin film containing a fluorescent organic compound or a phosphorescent organic compound is sandwiched between an anode and a cathode. In the organic light-emitting device, a hole (positive hole) and an electron are injected into the thin film containing the fluorescent organic compound or the phosphorescent organic compound from the electrodes. When the hole and the electron are recombined with each other in the thin film, an exciton of the fluorescent organic compound or the phosphorescent organic compound is produced. When this exciton returns to its ground state, the organic light-emitting device emits light.

The recent organic light-emitting device has remarkably advanced, and makes it possible to produce a thin and lightweight organic light-emitting device which has high brightness at low applied voltage, various emission wavelengths and high speed response. Thus, the organic light-emitting device has a possibility that it can be employed for wide-ranging applications.

However, under the present conditions, the organic light-emitting device needs to acquire a light output with higher brightness or higher conversion efficiency. In addition, the organic light-emitting device still has many problems in durability. For example, the device undergoes changes over time associated with its long-term use or is degraded by atmospheric gas containing oxygen, humidity and the like. Furthermore, the organic light-emitting device needs to emit lights of blue, green and red having high color purity when the device is applied to a full color display or the like. However, the organic light-emitting device in which these problems have been sufficiently solved has not been provided.

A method of employing a dibenzo[c,g]fluorene compound as a material constituting an organic light-emitting device is proposed so as to solve the afore-mentioned problems. The examples of the dibenzo[c,g]fluorene compound and the organic light-emitting device using same are disclosed in WO 2003/051092, US 2004/0131880, and Synthesis, photophysics and electroluminescence of poly(dibenzofluorene)s (Wei-Zhi Wang et al. Macromolecular Rapid Communications, Vol. 27, No. 14, p. 1142 (2006)). WO 2003/051092 discloses a compound which is substituted with a hole-transporting heterocyclic group such as an oxadiazole group, a thiadiazole group, a triazole group, a diarylamine group and a carbazole group at the 5- and 9-positions of the skeleton of a dibenzo[c,g]fluorene.

In addition, US 2004/0131880 discloses a compound which is substituted with a heterocyclic group such as thiophene and carbazole at the 5- and 9-positions of the skeleton of a dibenzo[c,g]fluorene.

DISCLOSURE OF THE INVENTION

The present invention has been made to solve the afore-mentioned problems of prior art.

An object of the present invention is to provide a new compound having a dibenzo[c,g]fluorene skeleton. Another object of the present invention is to provide an organic light-emitting device which efficiently emits light with high brightness and has durability.

The dibenzo[c,g]fluorene compound according to the present invention is a compound having two dibenzo[c,g]fluorene skeletons, which is represented by the following general formula [1]:

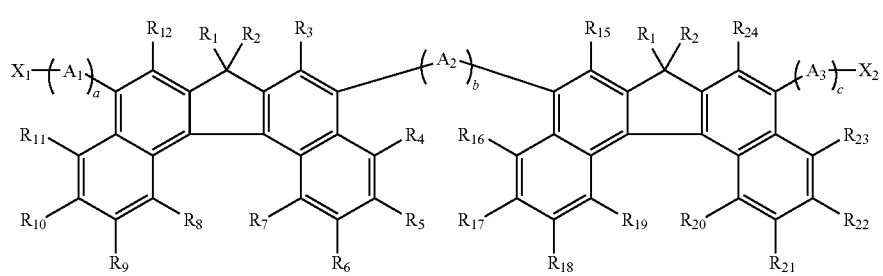

(In the above formula [1], $X_1$ and $X_2$ each represent a hydrogen atom, a substituted or unsubstituted aryl group, or a substituted or unsubstituted alkyl group, and may be the same or different; $A_1$ to $A_3$ each represent a substituted or unsubstituted arylene group, and may be the same or different; $R_1$ to $R_{24}$ each represent a hydrogen atom, or a substituted or unsubstituted alkyl group, and may be the same or different; a, b and c are each an integer of 0 to 4, provided that a+b+c is 0 or more and 4 or less; when a is 2 or more, $A_1$'s may be the same or different; when b is 2 or more, $A_2$'s may be the same or different; and when c is 2 or more, $A_3$'s may be the same or different.)

The present invention can provide a new compound having a dibenzo[c,g]fluorene skeleton. The present invention can also provide an organic light-emitting device which efficiently outputs light with high brightness and has high durability.

Further features of the present invention will become apparent from the following description of exemplary embodiments with reference to the attached drawings.

BEST MODES FOR CARRYING OUT THE INVENTION

Figure 1:
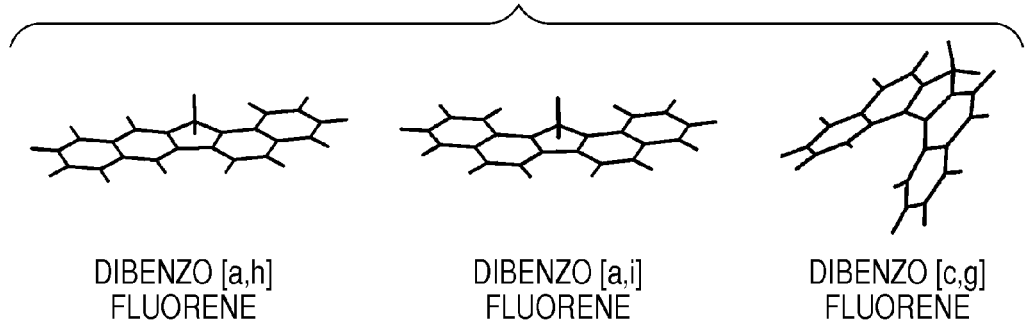
FIG. 1 is a view illustrating steric structures of isomers of dibenzofluorene.

The dibenzo[c,g]fluorene compound according to the present invention will be described in detail.

The dibenzo[c,g]fluorene compound according to the present invention is a compound having two dibenzo[c,g] fluorene skeletons, which is represented by the following general formula [1].

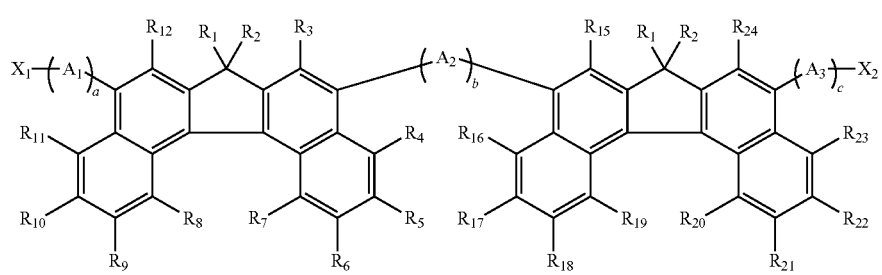

[1]

In formula [1], $X_1$ and $X_2$ each represent a hydrogen atom and a substituted or unsubstituted aryl group or a substituted or unsubstituted alkyl group. $X_1$ and $X_2$ are each preferably a hydrogen atom or a substituted or unsubstituted alkyl group.

The aryl groups represented by $X_1$ and $X_2$ include a phenyl group, a naphthyl group, an azulenyl group, an acenaphthylenyl group, an indacenyl group, a biphenyl group, a fluorenyl group, an anthryl group, a phenanthryl group, a pyrenyl group, a chrysenyl group, a benzofluorenyl group, a tetraphenyl group, a naphthacenyl group, a triphenylenyl group, a fluoranthenyl group, a picenyl group, a pentacenyl group, a perylenyl group, a benzofluoranthenyl group and a naphthofluoranthenyl group. However, of course, the aryl groups are not limited to these groups.

The alkyl groups represented by $X_1$ and $X_2$ include a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group and an adamantyl group. However, of course, the alkyl groups are not limited to these groups.

Substituents which may further be contained in the above described aryl group and alkyl group include an alkyl group such as a methyl group, an ethyl group, a propyl group, a tert-butyl group, an iso-butyl group, a sec-butyl group and a tert-butyl group, and an aryl group such as a phenyl group, a terphenyl group, a naphthyl group, a biphenyl group, a fluorenyl group, a phenanthryl group and a chrysenyl group. However, of course, the substituents are not limited to these groups.

In addition, $X_1$ and $X_2$ may be the same or different.

In formula [1], $A_1$ to $A_3$ each represent a substituted or unsubstituted arylene group.

The arylene groups represented by $A_1$ to $A_3$ include a phenylene group, a naphthylene group, an azulenylene group, an acenaphthylenylene group, an indacenylene group, a biphenylene group, a fluorenylene group, an anthrylene group, a phenanthrylene group, a pyrenylene group, a chrysenylene group, a benzofluorenylene group, a tetraphenylene group, a naphthacenylene group, a triphenylenylene group, a fluoranthenylene group, a picenylene group, a pentacenylene group, a perylenylene group, a benzofluoranthenylene group and a naphthofluoranthenylene group. However, of course, the arylene groups are not limited to these groups.

$A_2$ is preferably a substituent selected from a phenylene group, a biphenylene group, a terphenylene group, a naphthylene group, an anthrylene group, a phenanthrylene group, a pyrenylene group and a fluorenylene group.

A substituent which may further be contained in the above described arylene group includes an alkyl group such as a methyl group, an ethyl group, a propyl group, a tert-butyl group, an iso-butyl group, a sec-butyl group and a tert-butyl group, and an aryl group such as a phenyl group, a terphenyl group, a naphthyl group, a biphenyl group, a fluorenyl group, a phenanthryl group and a chrysenyl group. However, of course, the substituent is not limited to these groups.

In addition, $A_1$ to $A_3$ may be the same or different.

In formula [1], $R_1$ to $R_{24}$ each represent a hydrogen atom, or a substituted or unsubstituted alkyl group.

The alkyl groups represented by $R_1$ to $R_{24}$ include a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group and an adamantyl group. However, of course, the alkyl groups are not limited to these groups.

A substituent which may further be contained in the above described alkyl group includes an alkyl group such as a methyl group, an ethyl group, a propyl group, a tert-butyl group, an iso-butyl group, a sec-butyl group, and a tert-butyl group, and an aryl group such as a phenyl group, a terphenyl group, a naphthyl group, a biphenyl group, a fluorenyl group, a phenanthryl group and a chrysenyl group. However, of course, the substituent is not limited to these groups.

In addition, $R_1$ to $R_{24}$ may be the same or different.

In formula [1], a, b and c are each an integer of 0 to 4. It is preferable that a and b are 0. However, a+b+c is 0 or more and 4 or less.

When a is 2 or more, $A_1$'s may be the same or different.
When b is 2 or more, $A_2$'s may be the same or different.
When c is 2 or more, $A_3$'s may be the same or different.

Exemplary embodiments of a dibenzo[c,g]fluorene compound according to the present invention include the following embodiments:

(i) a and b are 0, and $X_1$ and $X_2$ each represent a hydrogen atom or a substituted or unsubstituted alkyl group; and (ii) $A_2$ is a substituent selected from a substituted or unsubstituted phenylene group, a substituted or unsubstituted biphenylene group, a substituted or unsubstituted terphenylene group, a substituted or unsubstituted naphthylene group, a substituted or unsubstituted anthrylene group, a substituted or unsubstituted phenanthrylene group, a substituted or unsubstituted pyrenylene group and a substituted or unsubstituted fluorenylene group.

Next, a method for synthesizing the dibenzo[c,g]fluorene compound according to the present invention will be described. The dibenzo[c,g]fluorene compound according to the present invention can be synthesized with reference to Tetrahedron Letters, Vol. 45, Issue 17, p. 3485 (2004), Journal of Chemical Society, p. 679 (1941), Macromolecular Rapid Communications, Vol. 27, No. 14, p. 1142 (2006), Bulletin of the Chemical Society of Japan, Vol. 62, No. 2, p. 439 (1989), European Journal of Organic Chemistry, Issue 4, p. 701 (1998) and the like.

Specifically, the dibenzo[c,g]fluorene compound can be synthesized through the following steps:

(I) Synthesis of a brominated product of a dibenzo[c,g] fluorene;

(II) Synthesis of a dibenzo[c,g]fluorene derivative; and (III) Synthesis of a dibenzo[c,g]fluorene compound formed by coupling of a bromine-containing compound such as a brominated product of a dibenzo[c,g]fluorene with an organic boron compound.

The brominated product of a dibenzo[c,g]fluorene to be synthesized by the step (I) can be synthesized by, for example, a method shown in Scheme 1 as below.

Scheme 1

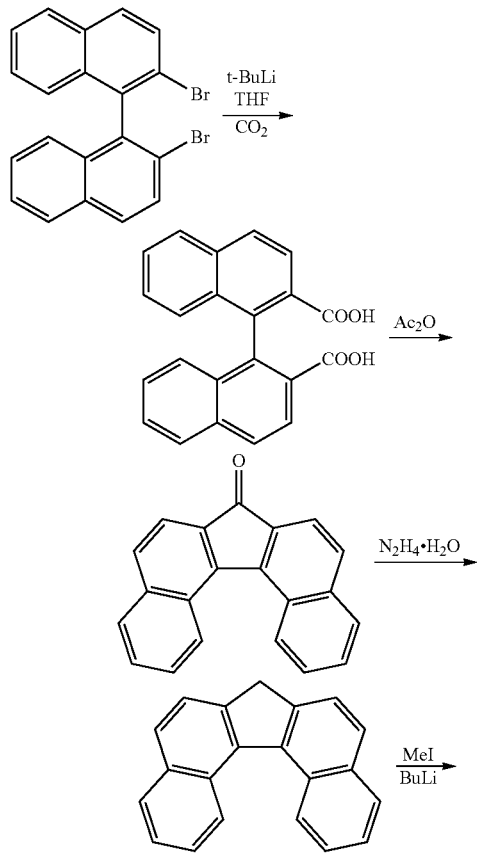

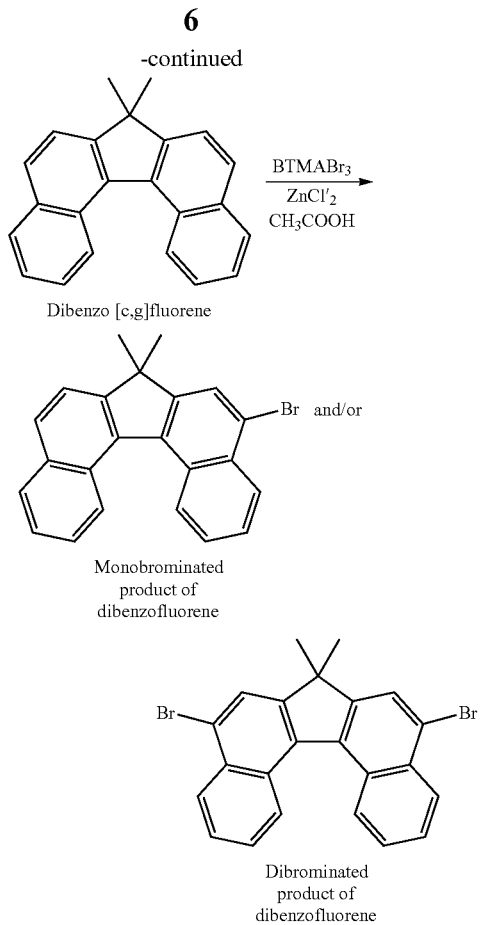

In the Scheme 1, the product can be controlled to be in the form of a monobrominated product of dibenzofluorene or the form of a dibrominated product of dibenzofluorene by controlling the equivalent ratio of benzyltrimethylammonium tribromide ($BTMABr_3$) which is a brominating agent.

Next, various dibenzo[c,g]fluorene derivatives to be synthesized in the step (II) can be synthesized by, for example, a method shown in Schemes 2 to 4 as below.

Scheme 2

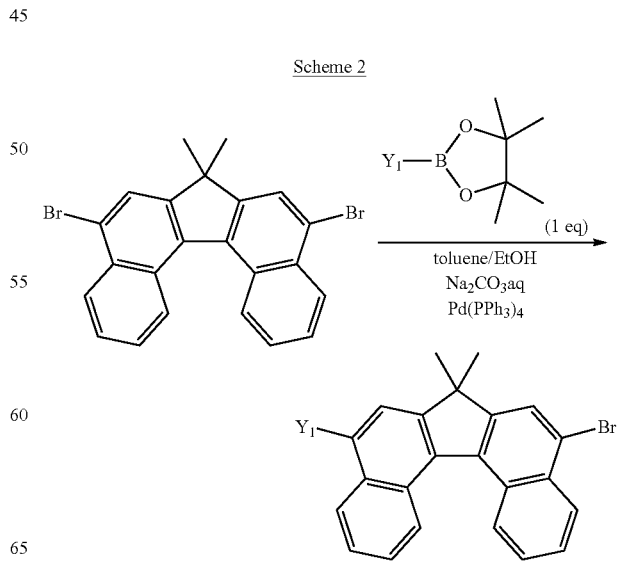

Scheme 3

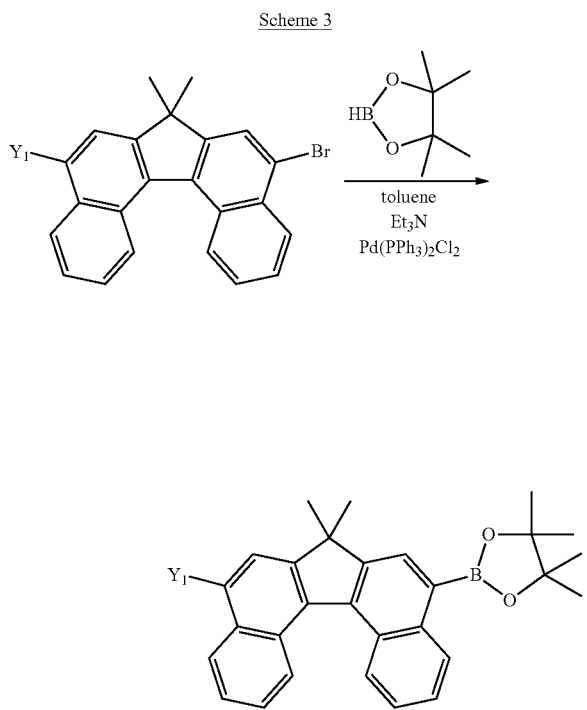

Scheme 4

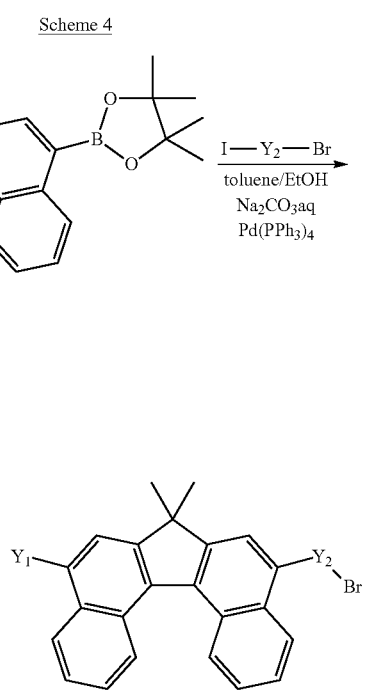

In Schemes 2 to 4, $Y_1$ represents a hydrogen atom, a substituted or unsubstituted alkyl group or a substituted or unsubstituted aryl group.

The alkyl group represented by $Y_1$ includes a methyl group, an ethyl group, an n-propyl group, an iso-propyl group, an n-butyl group, an iso-butyl group, a sec-butyl group, a tert-butyl group, an n-pentyl group, a neopentyl group, an n-hexyl group, an n-octyl group, an n-decyl group, an n-dodecyl group, a cyclopropyl group, a cyclobutyl group, a cyclopentyl group, a cyclohexyl group, a norbornyl group and an adamantyl group. However, of course, the alkyl group is not limited to these groups.

The aryl group represented by $Y_1$ includes a phenyl group, a naphthyl group, an azulenyl group, an acenaphthylenyl group, an indacenyl group, a biphenyl group, a fluorenyl group, an anthryl group, a phenanthryl group, a pyrenyl group, a chrysenyl group, a benzofluorenyl group, a tetraphenyl group, a naphthacenyl group, a triphenylenyl group, a fluoranthenyl group, a picenyl group, a pentacenyl group, a perylenyl group, a benzofluoranthenyl group and a naphthofluoranthenyl group. However, of course, the aryl group is not limited to these groups.

Substituents which may be contained in the above described alkyl group and aryl group include an alkyl group such as a methyl group, an ethyl group, a propyl group, a tert-butyl group, an iso-butyl group, a sec-butyl group and a tert-butyl group, and an aryl group such as a phenyl group, a terphenyl group, a naphthyl group, a biphenyl group, a fluorenyl group, a phenanthryl group and a chrysenyl group. However, of course, the substituents are not limited to these groups.

In Scheme 4, $Y_2$ represents a substituted or unsubstituted arylene group.

The arylene group represented by $Y_2$ includes a phenylene group, a naphthylene group, an azulenylene group, an acenaphthylenylene group, an indacenylene group, a biphenylene group, a fluorenylene group, an anthrylene group, a phenanthrylene group, a pyrenylene group, a chrysenylene group, a benzofluorenylene group, a tetraphenylene group, a naphthacenylene group, a triphenylene group, a fluoranthenylene group, a picenylene group, a pentacenylene group, a perylenylene group, a benzofluoranthenylene group and a naphthofluoranthenylene group. However, of course, the arylene group is not limited to these groups.

A substituent which may be contained in the above described arylene group includes an alkyl group such as a methyl group, an ethyl group, a propyl group, a tert-butyl group, an iso-butyl group, a sec-butyl group and a tert-butyl group, and an aryl group such as a phenyl group, a terphenyl group, a naphthyl group, a biphenyl group, a fluorenyl group, a phenanthryl group and a chrysenyl group. However, of course, the substituent is not limited these groups.

The starting compound in the above described Scheme 2 is a dibrominated product of a dibenzofluorene synthesized in Scheme 1.

Next, dibenzo[c,g]fluorene compounds to be synthesized in the step (III) can be synthesized by, for example, methods shown in Schemes 5 to 7 as below. Two $Y_1$'s shown in compounds synthesized in the following Schemes 5 to 7 may be the same or different.

Scheme 5
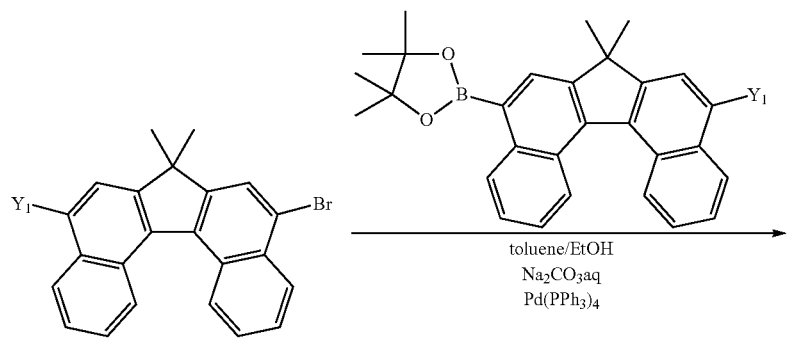
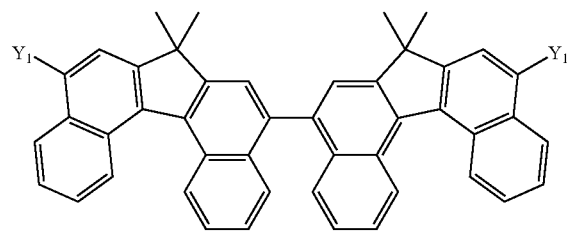
Scheme 6
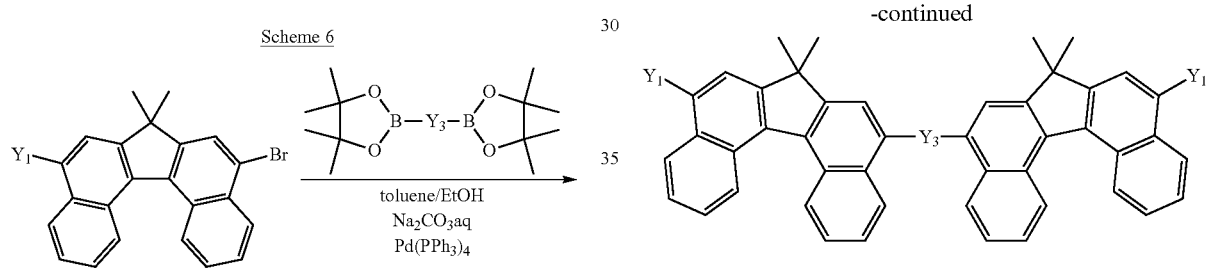
Scheme 7
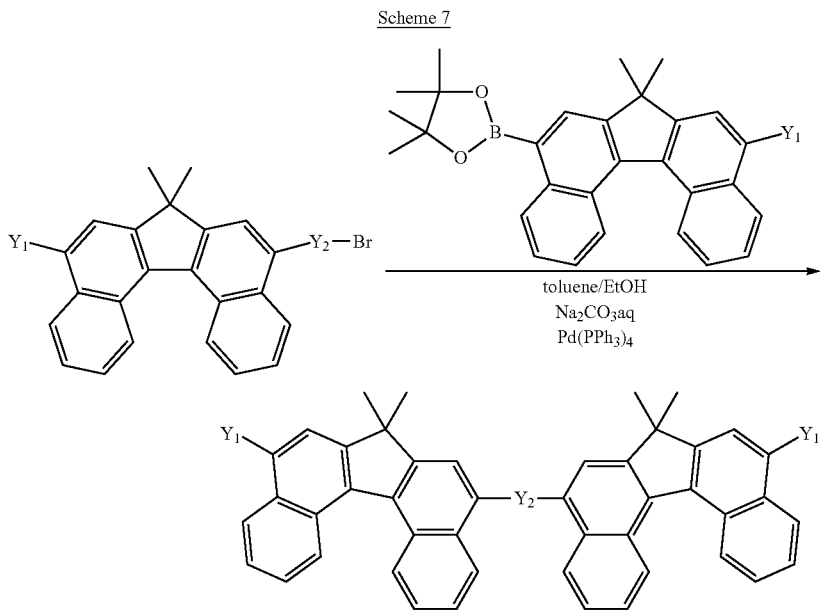

In Scheme 6, $Y_3$ represents a substituted or unsubstituted arylene group.

The arylene group represented by $Y_3$ includes a phenylene group, a naphthylene group, an azulenylene group, an acenaphthylenylene group, an indacenylene group, a biphenylene group, a fluorenylene group, an anthrylene group, a phenanthrylene group, a pyrenylene group, a chrysenylene group, a benzofluorenylene group, a tetraphenylene group, a naphthacenylene group, a triphenylene group, a fluoranthenylene group, a picenylene group, a pentacenylene group, a perylenylene group, a benzofluoranthenylene group and a naphthofluoranthenylene group. However, of course, the arylene group is not limited to these groups.

A substituent which may be contained in the above described arylene group includes an alkyl group such as a methyl group, an ethyl group, a propyl group, a tert-butyl group, an iso-butyl group, a sec-butyl group and a tert-butyl group, and an aryl group such as a phenyl group, a terphenyl group, a naphthyl group, a biphenyl group, a fluorenyl group, a phenanthryl group and a chrysenyl group. However, of course, the substituent is not limited to these groups.

The starting compound illustrated in the above illustrated Schemes 5 to 7 is a brominated product of a dibenzo[c,g]fluorene synthesized through the step (I) or is a derivative of a dibenzo[c,g]fluorene synthesized through the step (II).

The starting compound of the dibenzo[c,g]fluorene compound to be synthesized in the above described steps (I) to step (III) is 7,7-dimethyl dibenzo[c,g]fluorene, but the present invention is not limited to this.

As described above, the dibenzo[c,g]fluorene compound according to the present invention is a compound including only a hydrocarbon based on two dibenzo[c,g]fluorene skeletons.

In general, it is preferable that a compound to be used as a material constituting an organic light-emitting device contains no impurity. This is for the reason that when a molecule contains a heterocycle or a hetero atom, the molecule tends to contain ionic impurities more easily than a compound including only carbon and hydrogen (hydrocarbon compound) due to its high polarity, because the hetero atom in the molecule has an unpaired electron. On the other hand, the dibenzo[c,g]fluorene compound according to the present invention is a compound including only carbon and hydrogen, so ionic impurities are easily removed from the compound. For this reason, the compositional feature of the dibenzo[c,g]fluorene compound according to the present invention becomes a great advantage when being used for a material constituting an organic light-emitting device. Specifically, it is considered that the dibenzo[c,g]fluorene compound composed of a hydrocarbon, employing hydrocarbon groups such as aryl groups and alkyl groups for substituents in its skeleton, is a material exhibiting more adequate light-emitting efficiency and higher durability than that employing heterocyclic groups and hetero atoms for the substituents.

In addition, a heterocycle group or a hetero atom generally exhibits stronger electron-donating properties or electron-attracting properties than a hydrocarbon. Therefore, the energy level of HOMO-LUMO in the molecule significantly increases or decreases. On the other hand, the dibenzo[c,g]fluorene compound according to the present invention includes only carbon and hydrogen, so the energy level of HOMO-LUMO symmetrically changes according to the conjugate length of the molecule. This feature is a suitable characteristic for a host which plays both roles of electron injection and hole injection.

When a substituent with which the dibenzo[c,g]fluorene skeleton is substituted is an aryl group, the substituent is not particularly limited, but is preferably a substituent having 4 or less rings in total from the viewpoint of film-forming properties and molecular weight when considering that the film is formed by a sublimation refining method or a vapor deposition method. For instance, the substituent includes a substituent selected from a phenylene group, a biphenylene group, a terphenylene group, a naphthylene group, an anthrylene group, a phenanthrylene group, a pyrenylene group and a fluorenylene group.

The steric structure of an isomer of a dibenzofluorene will now be discussed on the basis of calculation with the use of Chem 3D Ultra. FIG. 1 is a view illustrating the steric structures of various isomers of the dibenzofluorene derived from the calculation with the use of Chem 3D Ultra (manufactured by CambridgeSoft Co.). FIG. 1 illustrates that a dibenzo[a,h]fluorene and a dibenzo[a,i]fluorene have planar structures, but in contrast to this, a dibenzo[c,g]fluorene takes a helical structure as a whole. The reason why the dibenzo[c,g]fluorene forms such a helical structure as illustrated in FIG. 1 is considered to be that hydrogen at the 1-position and hydrogen at the 13-position in the skeleton repel each other, so that the skeleton itself is distorted. Therefore, the dibenzo[c,g]fluorene skeleton is large in steric hindrance, and hence, is considered to be a material high in amorphism.

Accordingly, when the dibenzo[c,g]fluorene compound according to the present invention is used as a guest of a light-emitting layer, it is considered that the compound can be doped in a high concentration due to large steric hindrance which the compound itself has. In contrast to this, a compound in which a conjugated plane has a planar structure, for instance, pyrene, is known not only to easily take a laminated structure and easily cause concentration quenching, but also to cause excimer light emission in addition to a monomer light emission. Here, when the excimer light emission has occurred, the compound forms a band having a smaller energy than that of the monomer. Because of this, the energy level during the excimer light emission becomes an energy trap, which results in decreasing light-emitting efficiency. Besides, when the excimer light emission has occurred, the wavelength of emitted light also becomes long, so if a compound which causes the excimer light emission was used for a material constituting an organic light-emitting device, the color is hard to adjust. As described above, a molecule like pyrene, which has high planarity and causes the excimer light emission, cannot inhibit the concentration quenching and the excimer light emission, unless a bulky substituent was attached to the molecule.

On the other hand, the dibenzo[c,g]fluorene compound according to the present invention does not have a planar skeleton because the compound itself has large steric hindrance, as is illustrated in FIG. 1. For this reason, even if the compound was not substituted with a bulky substituent, the compound can be expected to show an effect of inhibiting the concentration quenching and the excimer light emission. As a result, the compound can be doped in a high concentration, and can improve the performance of an organic light-emitting device.

The dibenzo[c,g]fluorene compound according to the present invention is relatively shallower in HOMO among hydrocarbon-based aromatic compounds having approximately the same band gap. In order to prove this, HOMO, LUMO and a band gap (BG) of each of the compounds according to the present invention and similar compounds were determined. As a result, the values as shown in the following Table 1 were obtained. In the Table 1, the values of HOMO's were determined with a photoelectron spectrometer AC-2 (manufactured by Riken Keiki Co., Ltd.), and the values of LUMO's were determined from band gaps determined with an ultraviolet spectrophotometer.

TABLE 1

| | Structure of compound | HOMO | LUMO | BG |
|---|---|---|---|---|
| No. 1 | | 5.84 eV | 2.43 eV | 3.41 eV |
| No. 2 | | 5.75 eV | 2.76 eV | 2.99 eV |
| No. 3 | | 5.69 eV | 2.76 eV | 2.93 eV |
| No. 4 | | 5.86 eV | 2.66 eV | 3.20 eV |
| No. 5 | | 5.72 eV | 2.77 eV | 2.95 eV |
| No. 6 | | 5.71 eV | 2.76 eV | 2.95 eV |

Table 1 shows that the dibenzo[c,g]fluorene compounds (No. 3 and No. 6) according to the present invention each have a comparatively shallower HOMO level. Therefore, when the dibenzo[c,g]fluorene compound is used as a host of the light-emitting layer, a driving voltage can be decreased because a barrier of hole injection toward a light-emitting layer from a hole injecting/transporting layer is lowered. Accordingly, when the hole injection is desired to be promoted, a carrier balance which is one cause of the degradation of the organic light-emitting device is improved by using the dibenzo[c,g] fluorene compound according to the present invention, so the life of the organic light-emitting device can be expected to be extended. The dibenzo[c,g]fluorene compound according to the present invention can make its HOMO level shallow while keeping the dimension of the band gap. For this reason, the efficiency of energy transfer from a host to a guest becomes also adequate. As a result, the organic light-emitting device can also be expected to be provided with high efficiency.

In addition, the dibenzo[c,g]fluorene compound according to the present invention is large in steric hindrance (having no planar structure) due to the distortion of the skeleton itself, consequently inhibits the concentration quenching of a guest, and can be doped in a high concentration. The dibenzo[c,g] fluorene compound also has large amorphism due to the distortion of the skeleton itself, and accordingly can form a light-emitting layer having an adequate film characteristic.

Figure 2A:
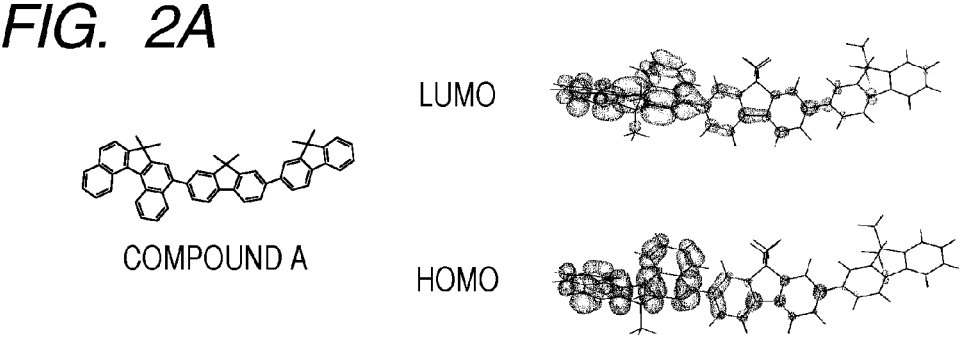
FIG. 2A is a view illustrating the calculation result of molecular orbits in a compound (Compound A) having one dibenzo[c,g]fluorene skeleton.
Figure 2B:
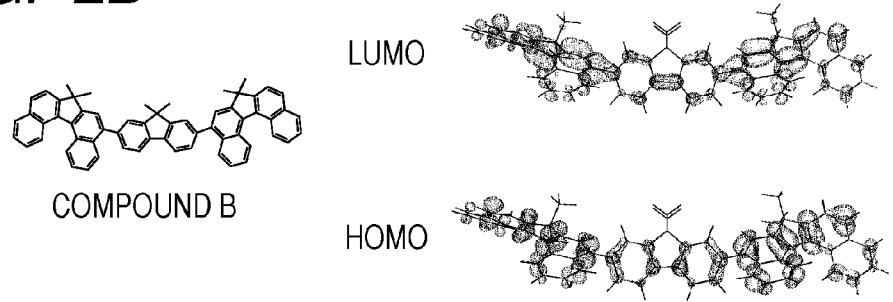
FIG. 2B is a view illustrating the calculation result of molecular orbits in a compound (Compound B) having two dibenzo[c,g]fluorene skeletons.

The dibenzo[c,g]fluorene compound according to the present invention has two dibenzo[c,g]fluorene skeletons. The reason for having two dibenzo[c,g]fluorene skeletons will be discussed on the basis of molecular orbit calculation. FIG. 2A and FIG. 2B are views illustrating the calculation results of molecular orbits in a compound (Compound A) having one dibenzo[c,g]fluorene skeleton and a compound (Compound B) having two dibenzo[c,g]fluorene skeletons, respectively. The molecular orbit calculation is carried out by using a nonempirical molecular orbit calculation program (Gaussian) and on the basis of a basis function (B3PW91/LANL2DZ).

It is understood that electrons in both HOMO and LUMO of the Compound A having one dibenzo[c,g]fluorene skeleton are distributed locally in a dibenzo[c,g]fluorene site, as is illustrated in FIG. 2A. Because of this, it can be said that the Compound A has a factor for suppressing the mobility of a carrier. On the other hand, as illustrated in FIG. 2B, it is understood that the Compound B having two dibenzo[c,g] fluorene skeletons has electrons distributed widely over the whole molecule in both HOMO and LUMO. Accordingly, it can be said that the dibenzo[c,g]fluorene compound according to the present invention has two dibenzo[c,g]fluorene skeletons as in the Compound (B), thereby improving the mobility of a carrier.

The compound having high amorphism originally tends to decrease the mobility of a carrier due to the long distance between molecules. On the other hand, the dibenzo[c,g]fluorene compound according to the present invention has uniform electron distribution within the molecule. Because of this, the hopping probability of a carrier between molecules can be improved, so that both the high amorphism and the high mobility can be realized. Therefore, it is considered that when the Compound (B) corresponding to the present invention is selected as a host of a light-emitting layer, the driving voltage can be lowered as compared with the Compound A. That is, it is considered that the dibenzo[c,g]fluorene compound according to the present invention has the higher mobility of a carrier.

Furthermore, the dibenzo[c,g]fluorene compound according to the present invention can have various characteristics according to the configuration of the molecule. As for the configuration of the molecule, there are specifically three types as below.

(Type a) A compound in which dibenzo[c,g]fluorene skeletonsare directly connected to each other:

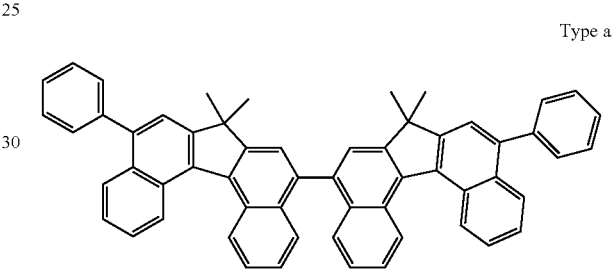

Type a

In Type a, two dibenzo[c,g]fluorene skeletons each having a distorted structure are directly connected to each other. Thereby, steric hindrance becomes larger. Because of this, Type a can be a material having higher amorphism and a more adequate film characteristic. Such a material can be doped in a higher concentration when being used as a material constituting a light-emitting layer.

(Type b) A compound having two terminal substituents which are different from each other:

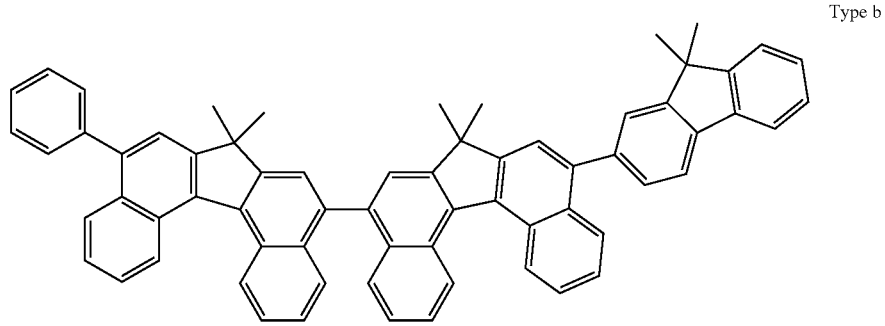 [SMILES: CC1(C)c2ccccc2-c2ccc(-c3cc4c(c5ccccc35)-c3c(cc(-c5cc6c(c7ccccc57)-c5c(cc(-c7ccccc7)c7ccccc57)C6(C)C)c5ccccc35)C4(C)C)cc21]

Type b

Like Type b, the whole molecule can be formed into an asymmetric configuration by appropriately selecting the terminal substituent so that two terminal substituents are different from each other. Type b is considered to be increased in amorphism because of its asymmetric molecular configuration.

(Type c) A compound which makes placed between two dibenzo[c,g]fluorene skeletons are connected through an arylene group and have the same substituents at their terminals

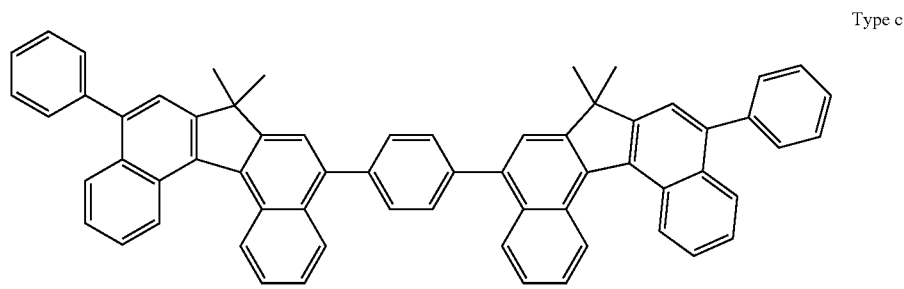 [SMILES: CC1(C)c2cc(-c3ccccc3)c3ccccc3c2-c2c1cc(-c1ccc(-c3cc4c(c5ccccc35)-c3c(cc(-c5ccccc5)c5ccccc35)C4(C)C)cc1)c1ccccc21]

Type c

In Type c, the molecule itself has adequate symmetry and accordingly has adequate crystallinity. Because of this, Type c can be a material having a higher carrier mobility capability.

As described above, in the dibenzo[c,g]fluorene compound according to the present invention, the molecule can be designed to have physical properties adjusted to some objective.

Specific structural formulas of organic compounds used in the present invention will be shown below. However, these formulas illustrate only representative examples, so the present invention is not limited thereto.

Group A (Type a)

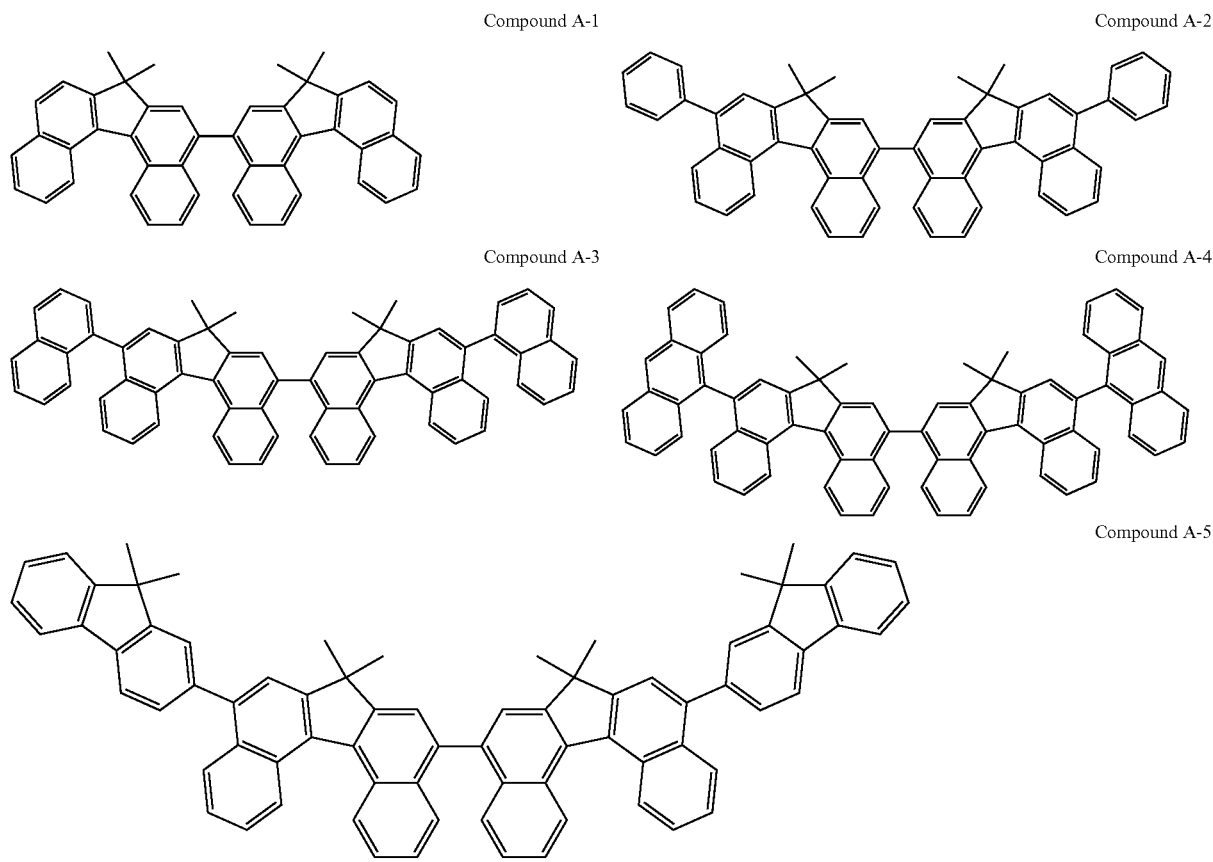

Compound A-1

Compound A-2

Compound A-3

Compound A-4

Compound A-5

-continued
Compound B-1
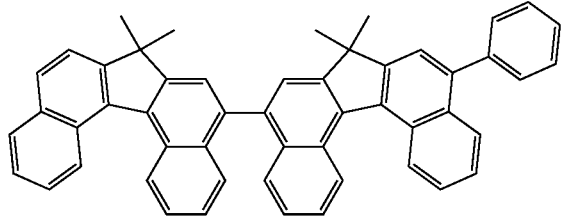
Group B (Type b)
Compound B-2
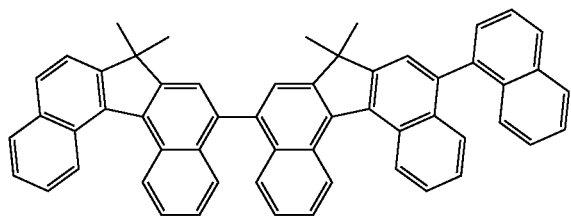
Compound B-3
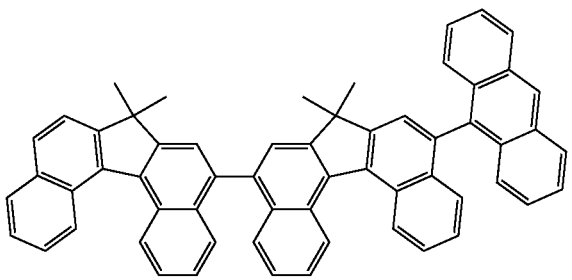
Compound B-4
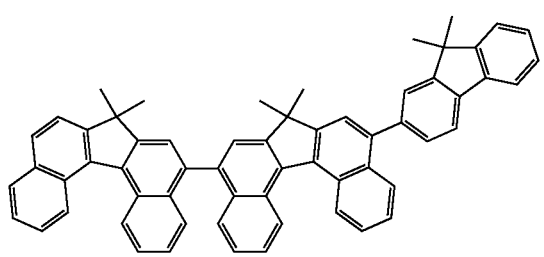
Compound B-5
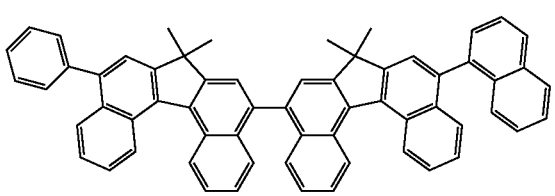
Compound B-6
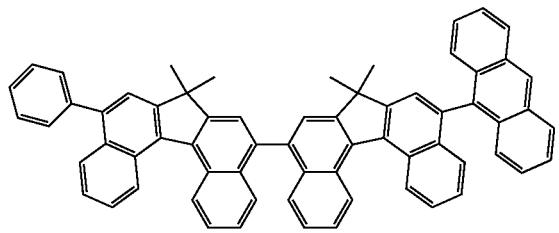
Compound B-7
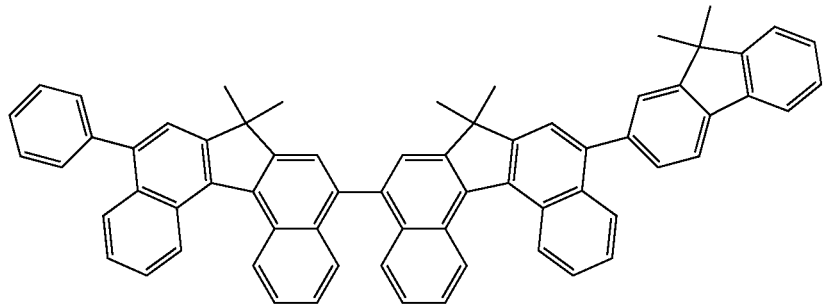
Compound B-8
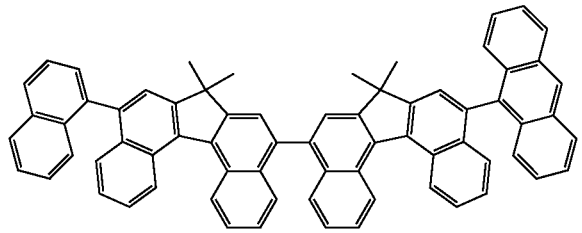

-continued
Compound B-9
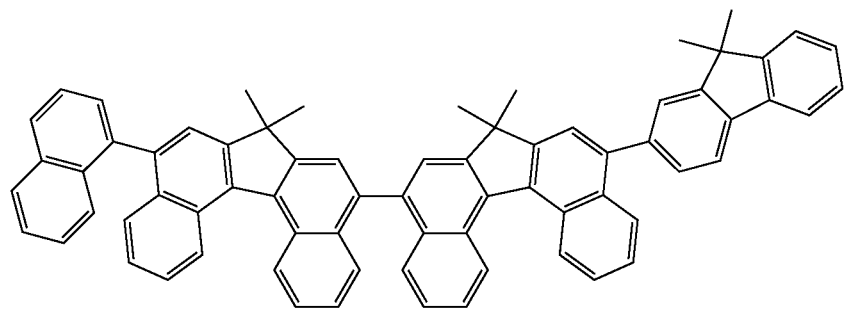
Compound B-10
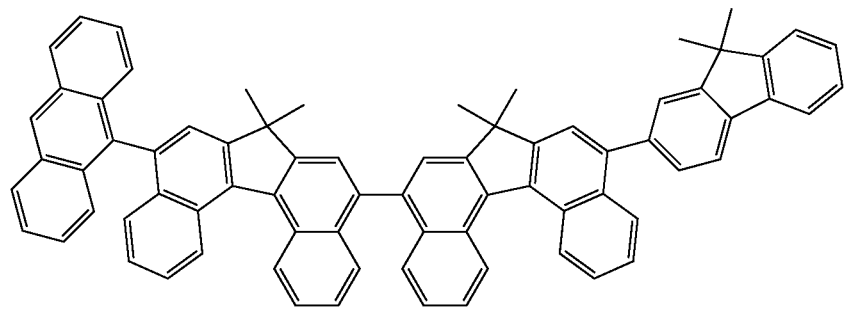
Group C (Type c)
Compound C-1
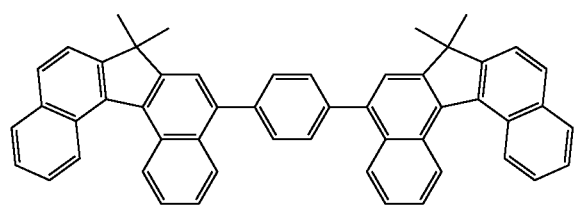
Compound C-2
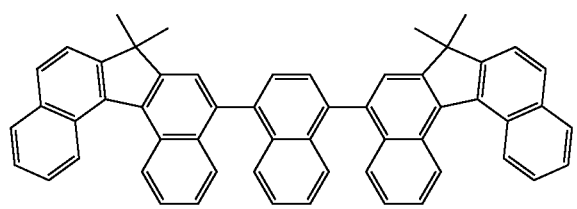
Compound C-3
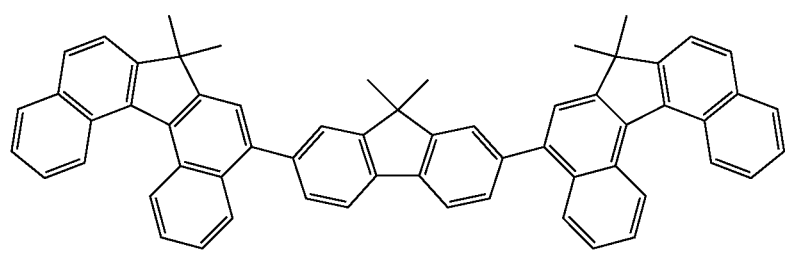
Group D (Type c)
Compound D-1
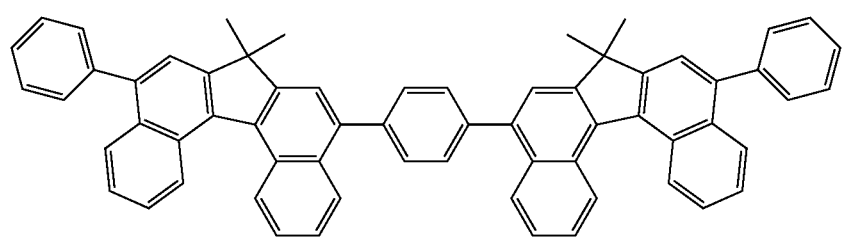

-continued
Compound D-2
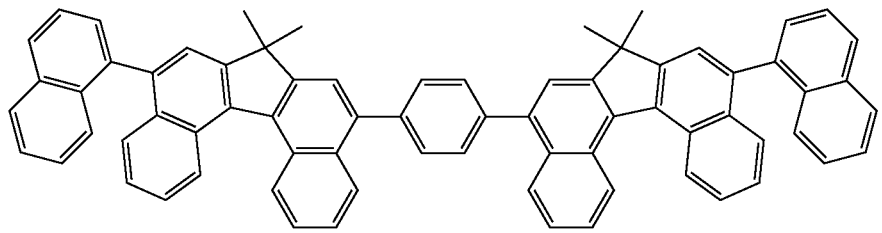
Compound D-3
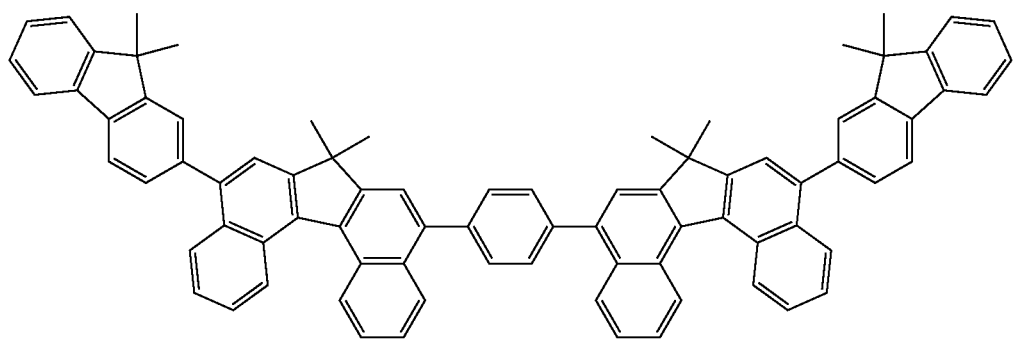
Compound D-4
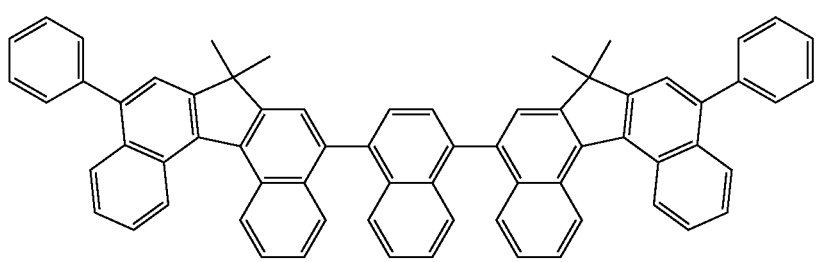
Compound D-5
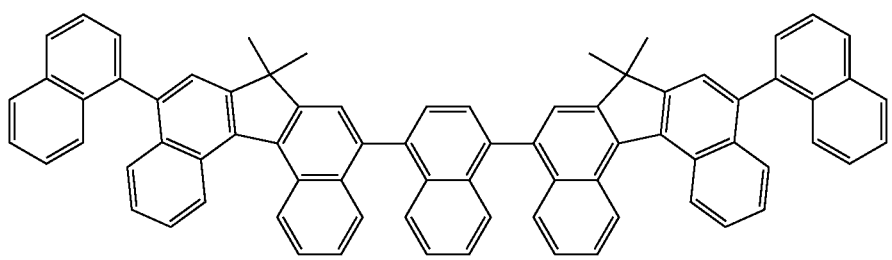
Compound D-6
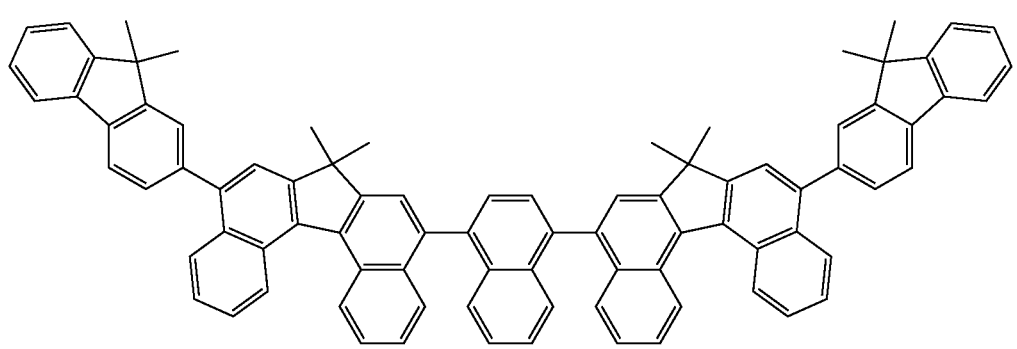

-continued
Compound D-7
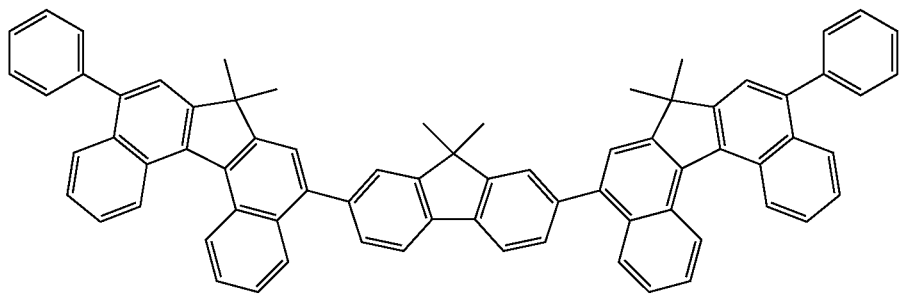
Compound D-8
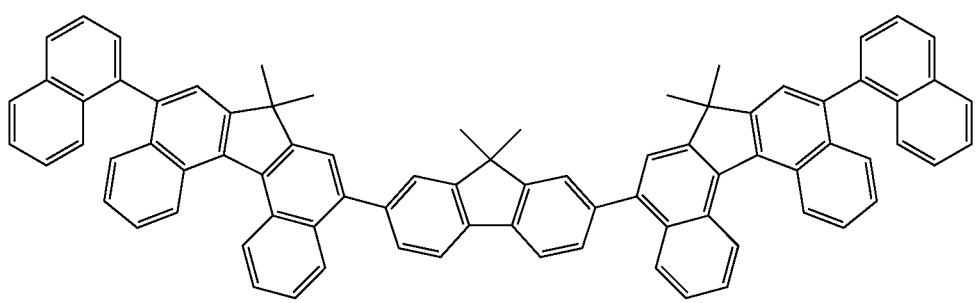
Compound D-9
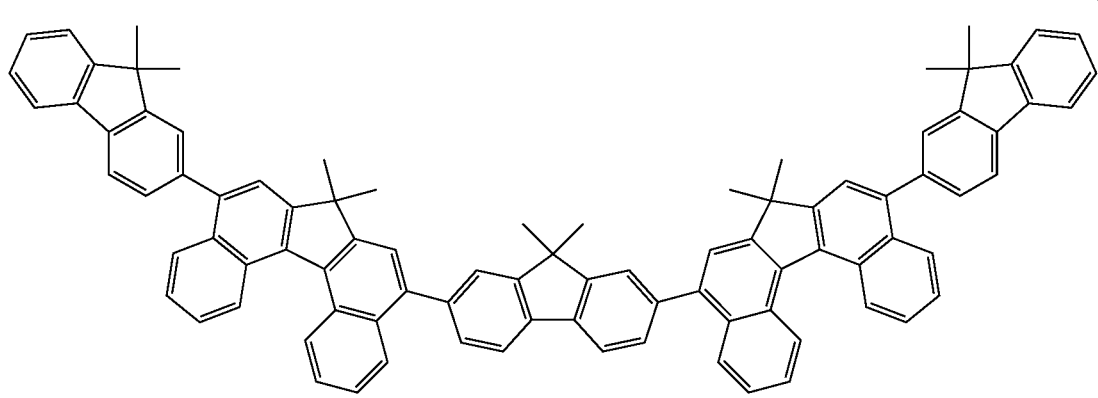
Group E (Type b)
Compound E-1
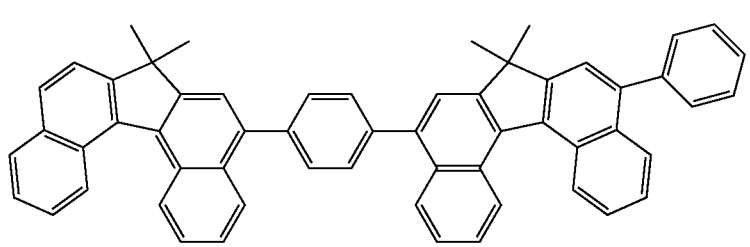
Compound E-2
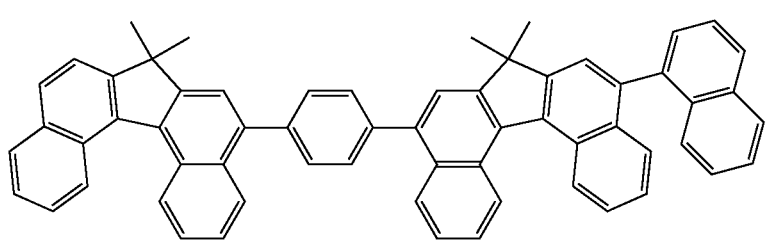

Compound E-3
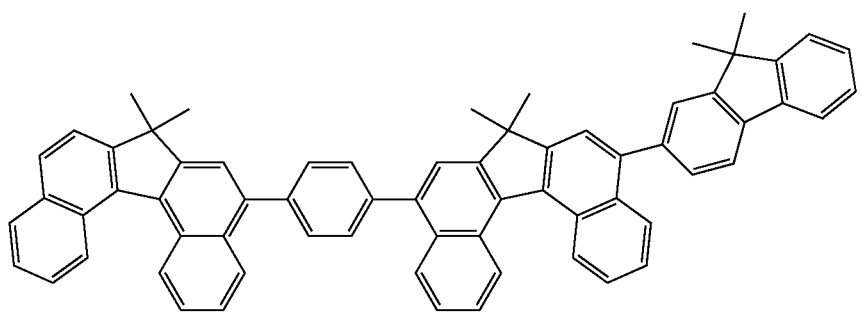
Compound E-4
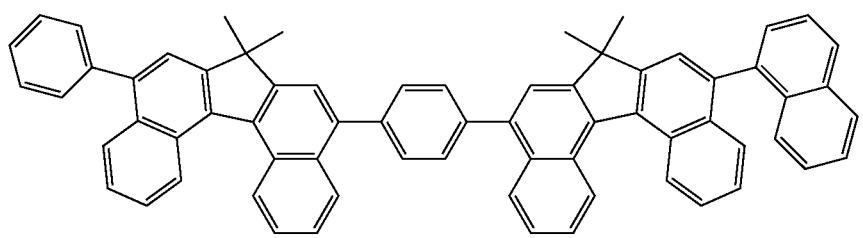
Compound E-5
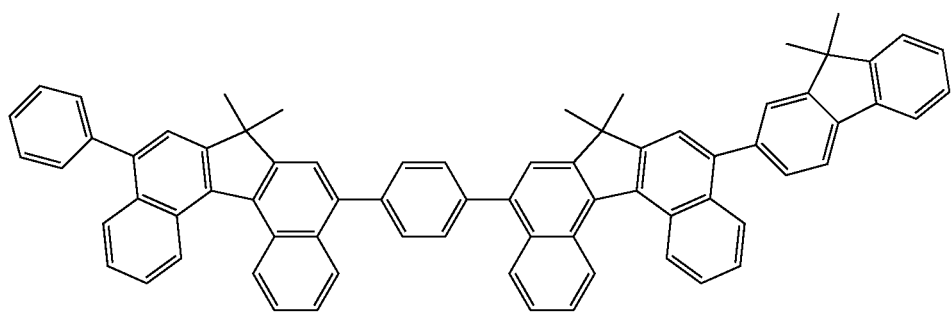
Compound E-6
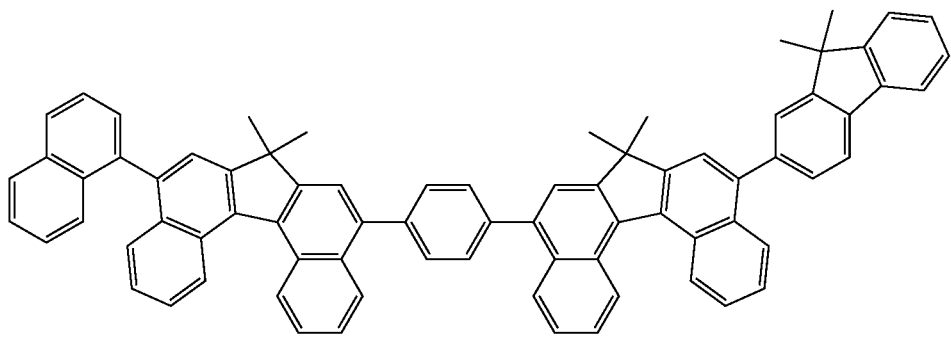
Compound E-7
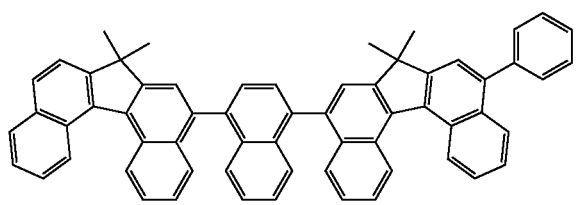

Compound E-8
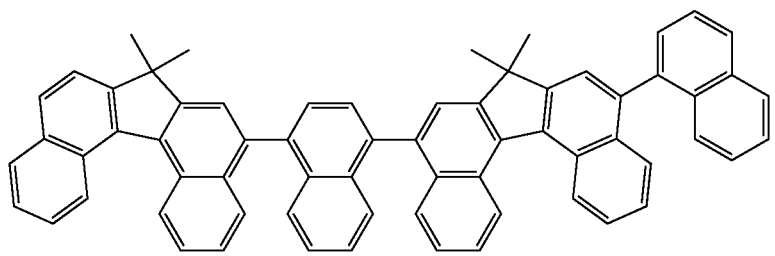
Compound E-9
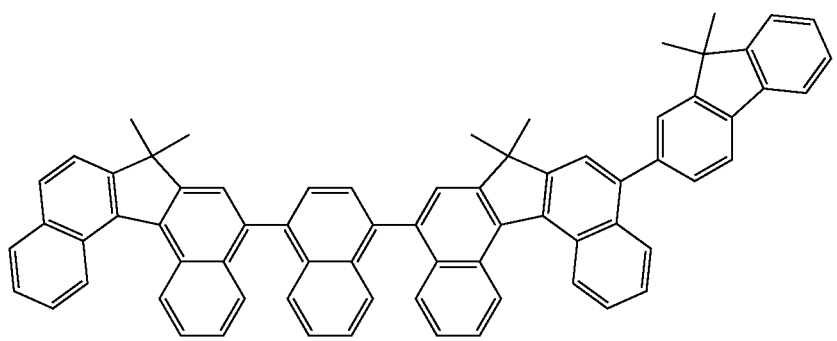
Compound E-10
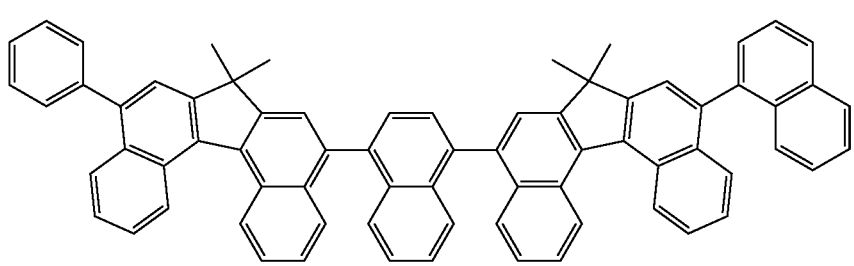
Compound E-11
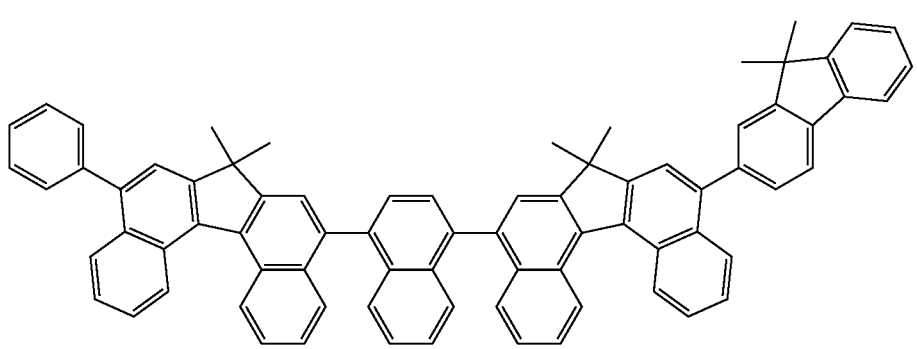
Compound E-12
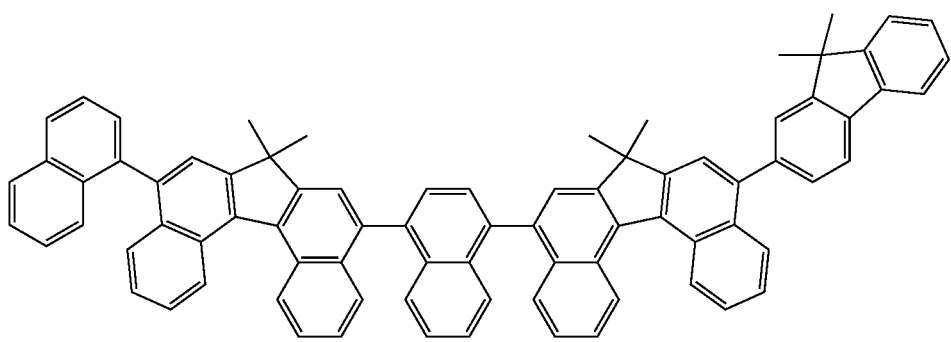

-continued
Compound E-13
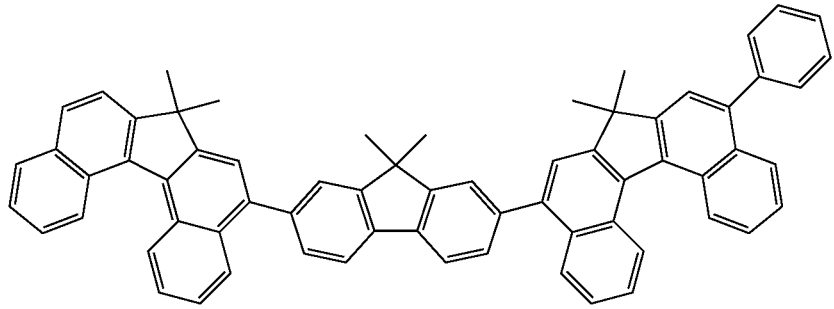
Compound E-14
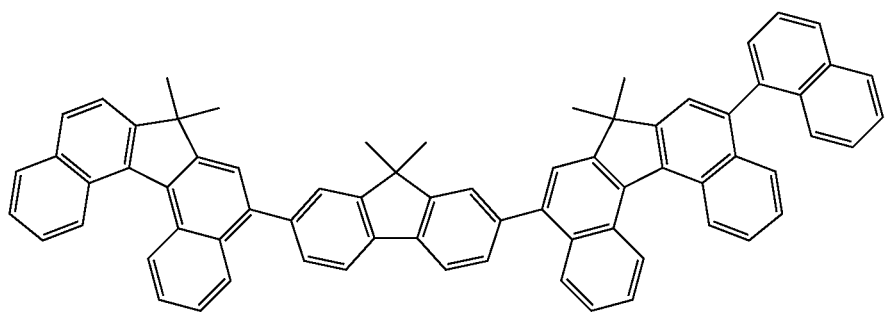
Compound E-15
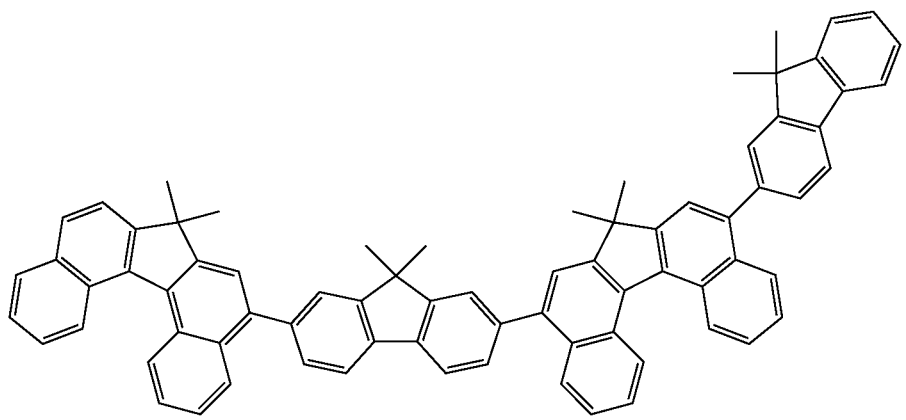
Compound E-16
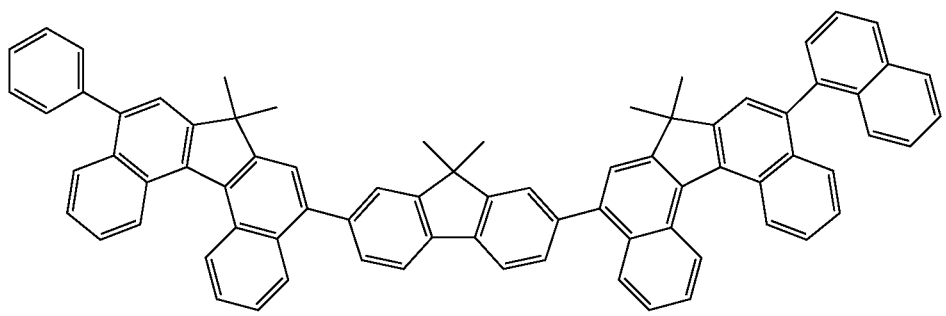

-continued

Compound E-17

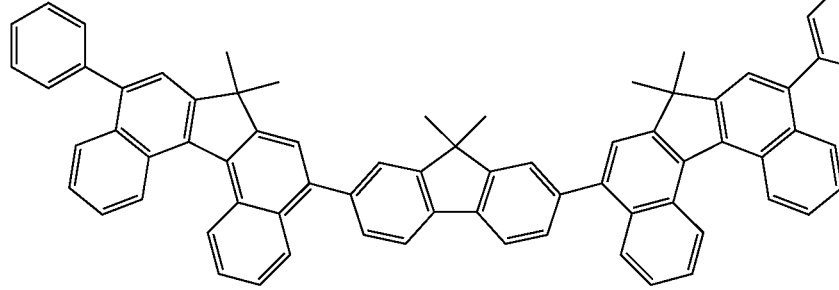

Compound E-18

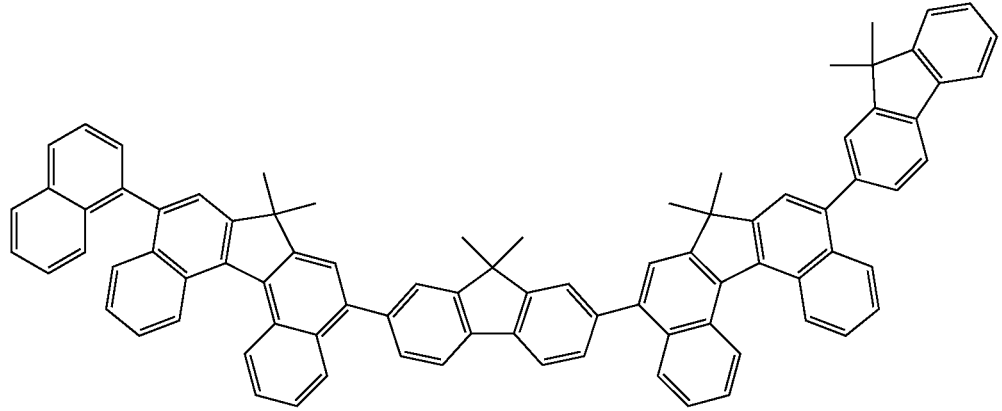

Next, the organic light-emitting device according to the present invention will be described below in detail.

The organic light-emitting device according to the present invention includes an anode, a cathode and an organic compound layer which is held between the anode and the cathode, and any one of the anode and the cathode is transparent or translucent. The organic light-emitting device according to the present invention can also be an electric-field light-emitting device which emits light when voltage is applied between the anode and the cathode.

The organic compound layer may be formed of a single layer or multiple layers. When the organic compound layer is formed of multiple layers, the multiple layers include functional layers each having a separate function. A specific example of the layer structure of the organic light-emitting device will be described below.

A first specific example is an example in which the organic light-emitting device includes a substrate, an anode, a light-emitting layer and a cathode in this order.

A second specific example is an example in which the organic light-emitting device includes a substrate, an anode, a hole transporting layer, an electron transporting layer and a cathode in this order. In this case, the light-emitting layer is the hole transporting layer and the electron transporting layer.

A third specific example is an example in which the organic light-emitting device includes a substrate, an anode, a hole transporting layer, a light-emitting layer, an electron transporting layer and a cathode in this order.

A fourth specific example is an example in which the organic light-emitting device includes a substrate, an anode, a hole injecting layer, a hole transporting layer, a light-emitting layer, an electron transporting layer and a cathode in this order.

A fifth specific example is an example in which the organic light-emitting device includes a substrate, an anode, a hole transporting layer, a light-emitting layer, a hole/exciton blocking layer, an electron transporting layer and a cathode in this order.

A sixth specific example is an example in which the organic light-emitting device includes a substrate, an anode, a hole transporting layer, a light-emitting layer, a hole/exciton blocking layer, an electron transporting layer, an electron injecting layer and a cathode in this order.

As shown in these examples, the organic compound layer to be arranged between the anode and the cathode may include various functional layers. The compound according to the present invention may be contained in at least one of these functional layers, or a particular functional layer may contain a plurality of compounds according to the present invention.

The structures described in the first to sixth specific examples are basic device structures, and the structure of the organic light-emitting device according to the present invention is not limited thereto. The organic light-emitting device according to the present invention can employ various layer structures such as a structure in which an insulating layer, an adhesion layer or an interference layer is provided in the interface between the electrode and the organic compound layer, a structure in which the hole transporting layer includes two layers having different ionization potentials, and a structure in which the light-emitting layer has a laminated structure of two or more layers, for instance.

The organic compound layer in which the dibenzo[c,g]fluorene compound according to the present invention is contained is preferably a light-emitting layer. The light-emitting layer containing the organic compound layer can be improved in light-emitting efficiency, keep light emission with high brightness for a long period of time, and decrease the deterioration of the organic light-emitting device due to energization.

When the dibenzo[c,g]fluorene compound according to the present invention is contained in the light-emitting layer, the light-emitting layer may include only the dibenzo[c,g]fluorene compound according to the present invention, but preferably include a host and a guest. The guest is a compound which shoulders main light emission in the light-emitting layer. On the other hand, the host is a compound which exists in the periphery of the guest as a matrix in the light-emitting layer, and mainly performs the transportation of a carrier and the supply of excitation energy to the guest.

Generally, when the light-emitting layer in the organic light-emitting device is formed of a carrier transporting host and a guest, a main process which leads to light emission includes the following several steps.

(1) transportation of electrons/holes in a light-emitting layer
(2) formation of excitons in a host
(3) transfer of excitation energy between host molecules
(4) transfer of excitation energy from host to guest Desired energy, transfer and light emission in the respective steps occur through various deactivation steps and competitions.

It goes without saying that it is necessary for improving the light-emitting efficiency of the organic light-emitting device to increase a light-emitting quantum yield of a light-emitting center material itself. On the other hand, a big problem is also raised in how efficiently energy can be transferred between a host and a host or between a host and a guest. In addition, the cause of deterioration in light emission due to energization which is a cause of decreasing the light-emitting efficiency of the organic light-emitting device is not presently clarified, but is presumed to relate to an environmental change of the light-emitting material originating in at least a light-emitting center material itself or molecules around the material.

The dibenzo[c,g]fluorene compound according to the present invention has the following characteristics:

(a) being difficult to taking in ionic impurities to be a carrier trap;
(b) having an appropriate value of HOMO (shallow HOMO); and
(c) having an adequate film characteristic.

It is expected from the above described characteristics that when the dibenzo[c,g]fluorene compound according to the present invention is used as a material constituting an organic light-emitting device, the device acquires higher efficiency and an extended life.

In addition, due to the afore-mentioned characteristics, the dibenzo[c,g]fluorene compound according to the present invention can be used as a component constituting a carrier transporting layer (hole transporting layer and/or electron transporting layer) and a light-emitting layer. The dibenzo[c,g]fluorene compound according to the present invention can be used as a material constituting the light-emitting layer.

It is effective to use the dibenzo[c,g]fluorene compound according to the present invention as a host or a guest contained in the light-emitting layer of the organic light-emitting device.

In the organic light-emitting device according to the present invention, when the dibenzo[c,g]fluorene compound according to the present invention is used as the host of the light-emitting layer, the guest can employ a fluorescent light-emitting compound and a phosphorescent light-emitting compound which are generally known, preferably a fluorescent light-emitting compound. The light-emitting layer can also contain a plurality of the fluorescent light-emitting compounds for the purpose of emitting lights having a plurality of colors from the light-emitting layer or aiding transmission of excitons or electrons.

The concentration of the guest is 0.01 wt % to 50 wt %, preferably 1 wt % to 30 wt %, based on the total amount of the materials constituting the light-emitting layer.

The guest may be uniformly contained in the whole layer formed from the host. The guest may be contained with a concentration gradient, and a region in which the guest is not contained may be provided by causing the guest to be partially contained in a particular region.

As described above, the organic light-emitting device according to the present invention contains the dibenzo[c,g]fluorene compound according to the present invention, particularly as a material constituting the light-emitting layer. However, a conventionally known hole transporting compound with a low molecular weight and a hole transporting compound with a high molecular weight, a light-emitting compound, an electron transport compound or the like can be also used together, as needed.

The example of these compounds will be described below.

A positive hole (hole) injecting/transporting material is preferably a material which satisfies such conditions that a hole is easily injected thereinto from an anode and the injected hole can be transported to a light-emitting layer therethrough, i.e., a material exhibiting a high mobility of a hole. A material with a low molecular weight and a material with a high molecular weight, which have hole injecting/transporting performance, include triarylamine derivatives, phenylenediamine derivatives, stilbene derivatives, phthalocyanine derivatives, porphyrin derivatives, poly(vinylcarbazole), poly(thiophene) and other electroconductive polymers. However, of course, the materials are not limited to these compounds.

A light-emitting material which is mainly involved with a light-emitting function includes a condensation cyclic compound (for instance, fluorene derivatives, pyrene derivatives, tetracene derivatives, 9,10-diphenylanthracene derivatives and rubrene), quinacridone derivatives, coumarin derivatives, stilbene derivatives and organoaluminum complexes such as tris(8-quinolinolate)aluminum, polymer derivatives such as poly(phenylenevinylene)derivatives, poly(fluorene)derivatives and poly(phenylene)derivatives, in addition to the dibenzo[c,g]fluorene compound according to the present invention. However, of course, the material is not limited thereto.

An electron injecting/transporting material may be arbitrarily selected from substances to which an electron is easily injected from a cathode and which can transport the injected electron to the light-emitting layer therethrough; and is selected in consideration of a balance with the carrier mobility of the hole transporting material and the like. A material having electron injecting/transporting performance includes oxadiazole derivatives, oxazole derivatives, pyrazine derivatives, triazole derivatives, triazine derivatives, quinoline derivatives, quinoxaline derivatives, phenanthroline derivatives and organoaluminum complexes. However, of course, the material is not limited to these compounds.

A material to be an anode has preferably a work function as large as possible. Usable materials include, for instance: an elemental metal such as gold, platinum, silver, copper, nickel, palladium, cobalt, selenium, vanadium and tungsten; alloys formed by combining two or more of these elemental metals; and metal oxides such as tin oxide, zinc oxide, indium oxide, indium tin oxide (ITO) and indium zinc oxide. An electroconductive polymer such as polyaniline, polypyrrole and polythiophene may be also used. These electrode materials may be used each singly or in a combination of two or more of them. In addition, the anode may include one layer or a plurality of layers.

On the other hand, a material to be a cathode has preferably a small work function. The material includes, for instance: an alkaline metal such as lithium, an alkaline earth metal such as calcium, and an elemental metal such as aluminum, titanium, manganese, silver, lead and chromium. Alternatively, alloys formed by combining two or more of these elemental metals can be also used. For instance, magnesium-silver, aluminum-lithium, aluminum-magnesium and the like can be used. Metal oxides such as indium tin oxide (ITO) can be also used. These electrode materials may be used each singly or in a combination of two or more of them. In addition, the cathode may include one layer or a plurality of layers.

A substrate to be used for the organic light-emitting device according to the present invention is not particularly limited, and usable materials include: a translucent substrate such as a substrate made from metal and a substrate made from ceramic; and a transparent substrate made from glass, quartz and a plastic sheet or the like. It is also possible to control the color of light by using a color filter film, a filter film for a fluorescent color conversion, a dielectric reflection film or the like, as the substrate.

The produced device may be also provided with a protective layer or a sealing layer for the purpose of preventing the produced device from coming into contact with oxygen, moisture and the like. The protective layer includes: an inorganic material film such as a diamond thin film, a metal oxide and a metal nitride; a polymer film such as a fluorine resin, polyethylene, a silicone resin and a polystyrene resin; and a photo-curable resin. It is also possible to package the device itself with an appropriate sealing resin after having coated the device with glass, a gas impervious film, a metal or the like.

The organic light-emitting device according to the present invention may be also prepared by producing a thin-film transistor (TFT) on a substrate, and connecting the device to the thin-film transistor.

In addition, as for a direction in which light of the device is taken out, a bottom emission structure in which light is taken out from a substrate side and a top emission structure in which light is taken out from an opposite side of a substrate can be adopted.

In the organic light-emitting device according to the present invention, a layer containing the dibenzo[c,g]fluorene compound according to the present invention and a layer formed from another organic compound are formed by the following methods. In general, a thin film is formed by a vacuum vapor-deposition method, an ionization vapor-deposition method, a sputtering method, a plasma or a known application method (for instance, a spin coating method, a dipping method, a casting method, an LB method and an ink-jet method) with the use of a solution in which the compound has been dissolved in an appropriate solvent. A layer formed by a vacuum vapor-deposition method or a solution application method is difficult to crystallize and is superior in stability over time. When a film is formed by an application method, the film can be also formed using the compound in combination with an appropriate binder resin.

The binder resin includes a polyvinyl carbazole resin, a polycarbonate resin, a polyester resin, an ABS resin, an acrylic resin, a polyimide resin, a phenol resin, an epoxy resin, a silicone resin and a urea resin. However, the binder is not limited to these resins. In addition, these binder resins may be used as a homopolymer or a copolymer, or may be used in a mixture of two or more of them. Furthermore, a known addition agent such as a plasticizer, an antioxidant and a UV absorber may be used together as needed.

EXAMPLES

The present invention will be described below more specifically by way of working examples, but is not limited thereto.

Example 1

Synthesis of Illustrative Compound (1)

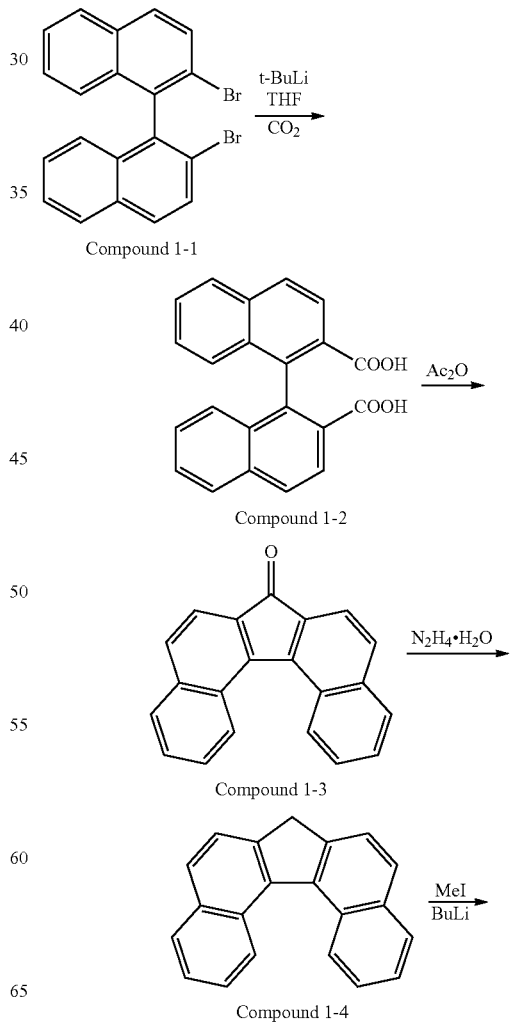

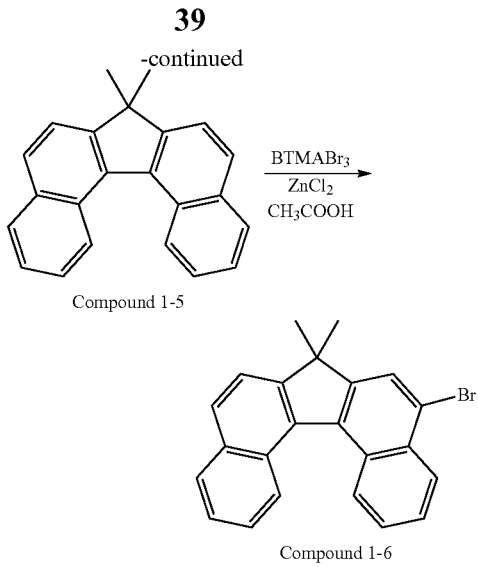

Compound 1-5

Compound 1-6

(1) Synthesis of Compound 1-6

(1-1) A reagent and a solvent shown below were charged into a reaction vessel to prepare a reaction solution.
Compound 1-1: 80 g (194.1 mmol)
Dehydrated THF: 800 ml The reaction solution was cooled to −78° C., the inside of the reaction vessel was set to be under the argon atmosphere, and then 70 ml (854 mol) of tert-BuLi was added dropwise into the reaction solution. Thereafter, the reaction solution was stirred for 1 hour while being kept at −78° C. Next, carbon dioxide was blown into the reaction solution, and subsequently, the temperature of the reaction solution was set at room temperature, and then, the reaction solution was stirred for 20 hours at that temperature. After the reaction was completed, 10% HCl was added to a water phase to acidify the solution, and an organic phase was extracted by chloroform. Subsequently, the organic phase was dried by anhydrous sodium sulfate, and the solvent was distilled away under reduced pressure to produce a crude product. Then, 44 g of Compound 1-2 (yield of 66%) was obtained by recrystallization-refining this crude product with the use of chloroform.

In addition, as a result of $^1$H-NMR measurement (300 MHz, DMSO), 14 protons belonged to the compound as below.
Carboxyl: 12.46 ppm (s, 2H)
Aryl: 8.31-6.86 ppm (m, 12H)

(1-2) A reagent and a solvent described below were charged into a reaction vessel to prepare a reaction solution.
Compound 1-2: 35 g (102.2 mmol)
Acetic anhydride: 350 ml The reaction solution was heated to 140° C., and was stirred at that temperature for 1 hour. After that, a residue obtained by concentrating the reaction solution under reduced pressure was heated at 300° C. for 3 hours, and a crude product was obtained. Then, this crude product was cooled, and was recrystallization-refined by toluene, and 4.0 g of Compound 1-3 was obtained. In addition, a filtrate produced when the crude product was recrystallized was concentrated under reduced pressure, then was refined by column chromatography (gel for chromatography: PSQ100 (produced by Fuji Silysia Chemical Ltd.), and developing solvent: hexane/ethyl acetate=5/1), and further 5.0 g of the Compound 1-3 was obtained. Accordingly, 9.0 g in total (yield of 32%) of the Compound 1-3 was obtained.

In addition, as a result of $^1$H-NMR measurement (300 MHz, CDCl$_3$), 12 protons belonged to the compound as below.
Aryl: 8.39-7.57 ppm (m, 12H)

(1-3) A reagent and a solvent shown below were charged into a tube to be sealed.
Compound 1-3: 9.0 g (32.1 mmol)
Hydrazine: 54 ml This tube was sealed to be a sealed tube, and then was heated and stirred at 180° C. for 15 hours. Next, the sealed tube was cooled, and then, the produced crystals were filtered. The crystals were washed with methanol, and 6.4 g of Compound 1-4 (yield of 75%) was obtained.

As a result of MALDI-TOF MS (matrix-assisted ionization deposition time-of-flight mass spectrometry), 280.7 which is m/z of this compound was confirmed.

In addition, as a result of $^1$H-NMR measurement (300 MHz, CDCl$_3$), 14 protons belonged to the compounds as below.
Aryl: 8.77-7.51 ppm (m, 12H)
Methylene: 4.13 ppm (s, 2H)

(1-4) A reagent and a solvent shown below were charged into a reaction vessel.
Compound 1-4: 6.4 g (24.0 mmol)
Dehydrated DMSO: 64 ml Next, reagents shown below were added into the reaction vessel to prepare a reaction solution.
Methyl iodide: 6.9 g (48 mmol)
Potassium iodide: 438 mg (2.63 mmol)

The reaction solution was cooled in an ice bath, and was set in an argon atmosphere, and then, 5.7 g (101.6 mmol) of potassium hydroxide was added to the reaction solution, and the reaction solution was stirred at the same temperature for 15 minutes. Next, the temperature of the reaction solution was returned to room temperature, and was stirred at room temperature for 15 hours. Thereafter, 2.3 g (16 mmol) of methyl iodide was added into the reaction solution. Subsequently, the reaction solution was heated to 60° C., and was stirred at that temperature for 7 hours. After that, the reaction solution was cooled, and an organic phase was extracted with ethyl acetate and was dried by anhydrous sodium sulfate, and then, the solvent was distilled away under reduced pressure, and a crude product was obtained. This crude product was refined by column chromatography (gel for chromatography: PSQ60 (produced by Fuji Silysia Chemical Ltd.), and developing solvent: hexane), and 4.4 g of Compound 1-5 (yield of 62%) was obtained.

As a result of MALDI-TOF MS (matrix-assisted ionization deposition time-of-flight time mass spectrometry), 294.8 which is m/z of this compound was confirmed.

In addition, as a result of $^1$H-NMR measurement (300 MHz, CDCl$_3$), 18 protons belonged to the compound as below.
Aryl: 8.73-7.49 ppm (m, 12H)
Methyl: 1.56, 1.51 ppm (s, 6H)

(1-5) A reagent and a solvent shown below were charged into a light shielding reaction vessel.
Compound 1-5: 4.1 g (11.0 mmol)
Chloroform: 600 ml Next, 4.29 g (11.0 mmol) of BTMABr$_3$ was added to the reaction solution while the reaction solution was cooled in an ice bath. Thereafter, the reaction vessel was sealed, and then was stirred for 30 minutes in a state of being cooled in the ice bath. After the reaction was completed, water was added to the reaction solution, to thereby separate the reaction solution into an aqueous phase and an organic phase, and the organic phase was collected. The organic phase was dried by anhydrous sodium sulfate, and the solvent was distilled away under reduced pressure to produce a crude product. This crude product was refined by column chromatography (PSQ60 (produced by Fuji Silysia Chemical Ltd.), and developing solvent: hexane), and 3.0 g of Compound 1-6 (yield of 73%) was obtained.

As a result of MALDI-TOF MS (matrix-assisted ionization deposition time-of-flight mass spectrometry), 373.7 which is m/z of this compound was confirmed.

In addition, as a result of $^1$H-NMR measurement (300 MHz, CDCl$_3$), 17 protons belonged to the compound as below.

Aryl: 8.69-7.53 ppm (m, 11H)
Methyl: 1.53 ppm (s, 6H)

(2) Synthesis of Compound 1-7

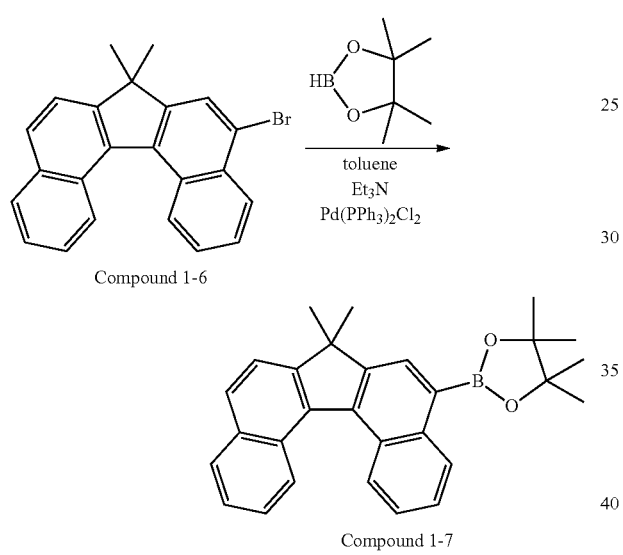

Compound 1-7

A reagent and a solvent shown below were charged into a reaction vessel.
Compound 1-6: 4 g (10.7 mmol)
Dehydrated toluene: 40 ml
Next, the inside of the vessel system was replaced with nitrogen, and then, reagents shown below were added into the reaction vessel to prepare a reaction solution.
4,4,5,5-Tetramethyl-[1,3,2]Dioxaborolane: 3.1 ml (21.4 mmol)
Triethylamine: 7.4 mg (53.4 mmol)
Bis(triphenylphosphine)palladium dichloride: 376 mg (0.54 mmol)
The reaction solution was heated to 100° C., and was stirred at that temperature for 6 hours. Thereafter, the reaction solution was cooled, and subsequently, an organic phase was extracted by toluene and was dried by anhydrous sodium sulfate, and then, the solvent was distilled away under reduced pressure to produce a crude product. This crude product was refined by column chromatography (gel for chromatography: BW300 (produced by Fuji Silysia Chemical Ltd.), and developing solvent: toluene), and was recrystallized in an ethanol/water mixed solution, and thus, 2.9 g of Compound 1-7 (yield of 64.6%) was obtained. 29 protons belonged to the compound.

In addition, as a result of $^1$H-NMR measurement, 29 protons belonged to the compound as below.

Aryl: 8.97 (dd, 1H), 8.73-8.71 ppm (m, 2H), 8.27 ppm (s, 1H), 7.99 ppm (d, 1H), 7.96 ppm (d, 1H), 7.70 ppm (d, 1H), 7.61-7.48 ppm (m, 4H)
Methyl: 1.64 ppm (s, 6H), 1.50 ppm (s, 12H)

(3) Synthesis of Illustrative Compound A-1

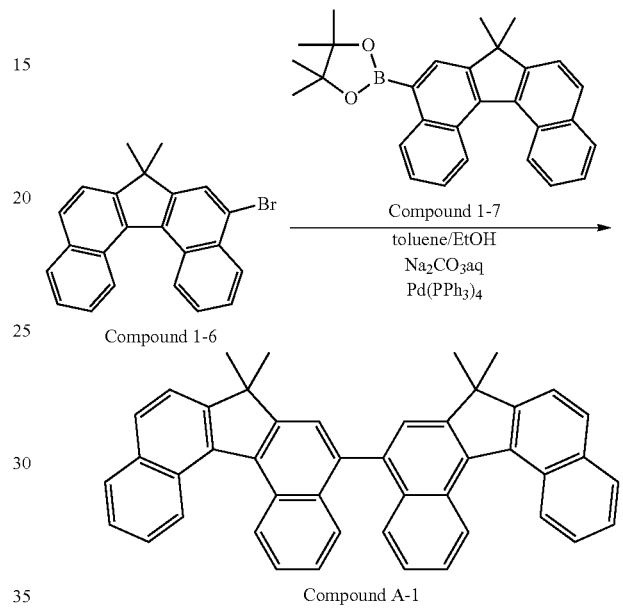

Compound A-1

A reagent and a solvent shown below were charged into a reaction vessel to prepare a reaction solution.
Compound 1-6: 188 mg (0.50 mmol)
Compound 1-7: 233 g (0.55 mmol)
Toluene: 10 ml
Ethanol: 5 ml
2 M sodium carbonate aqueous solution: 10 ml
Next, the inside of the reaction vessel was replaced with nitrogen, and then, 29 mg (0.025 mmol) of tetra(triphenylphosphine)palladium was added to the reaction vessel. The reaction solution was heated to 80° C., and was stirred at that temperature for 6 hours. Thereafter, the reaction solution was cooled, and subsequently, an organic phase was extracted by toluene and was dried by anhydrous sodium sulfate, and then, the solvent was distilled away under reduced pressure to produce a crude product. This crude product was refined by column chromatography (gel for chromatography: BW300 (produced by Fuji Silysia Chemical Ltd.), and developing solvent: heptane/toluene=1/4), and then, was recrystallized in a toluene/heptane mixture solution, and thus, 203 g of Compound A-1 (yield of 62.5%) was obtained.

As a result of $^1$H-NMR measurement (500 MHz, CDCl$_3$), 34 protons belonged to the compound as below.

Aryl: 8.87 (t, 4H), 8.06 ppm (d, 2H), 8.00 ppm (d, 2H), 7.86 ppm (s, 2H), 7.77 ppm (d, 2H), 7.72 ppm (d, 2H), 7.68-7.56 ppm (m, 6H), 7.39 ppm (t, 2H)
Methyl: 1.70 ppm (s, 6H), 1.69 ppm (s, 6H)

(4) Synthesis of Illustrative Compound C-3

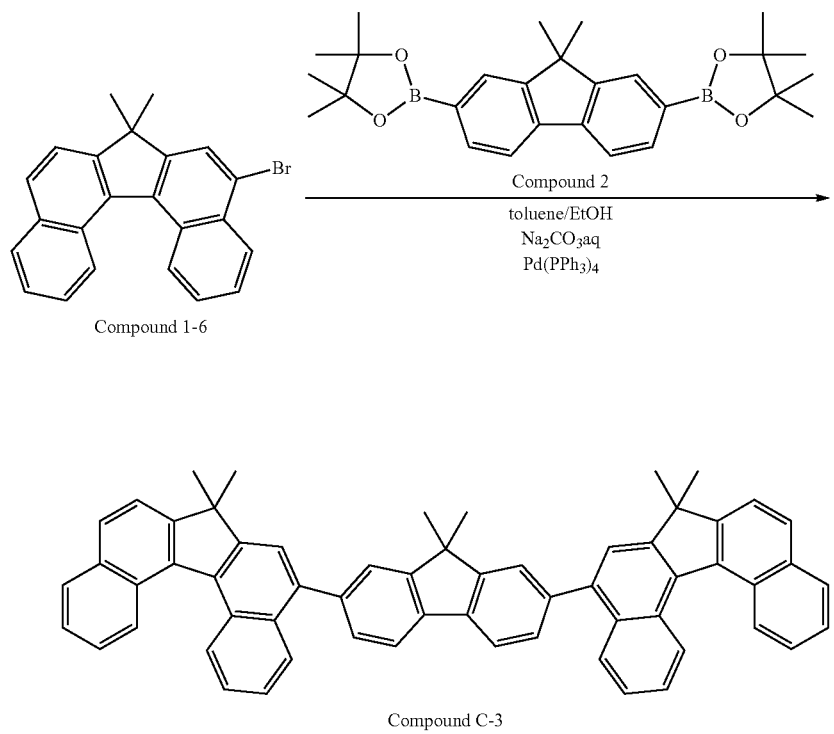

A reagent and a solvent shown below were charged into a reaction vessel.
Compound 1-6: 157 mg (0.42 mmol)
Compound 2: 102 mg (0.23 mmol)
Toluene: 10 ml
Ethanol: 5 ml
2 M sodium carbonate aqueous solution: 10 ml Next, the inside of the reaction vessel was replaced with nitrogen, and then, 23 mg (0.02 mmol) of tetra(triphenylphosphine)palladium was added to the reaction vessel to prepare a reaction solution. The reaction solution was heated to 80° C., and was stirred at that temperature for 6 hours. Thereafter, the reaction solution was cooled, and subsequently, an organic layer was extracted by toluene and was dried by anhydrous sodium sulfate, and then, the solvent was distilled away to produce a crude product. This crude product was refined by column chromatography (gel for chromatography: BW300 (produced by Fuji Silysia Chemical Ltd.), and developing solvent: heptane/toluene=1/3), and then, was recrystallized in ethanol, and thus, 110 g of Compound C-3 (yield of 66.8%) was obtained. As a result of $^1$H-NMR measurement (500 MHz, CDCl$_3$), 46 protons belonged to the compound.

Aryl: 8.83 (d, 2H), 8.79 ppm (d, 2H), 8.18 ppm (d, 2H), 8.04-7.97 ppm (m, 6H), 7.77-7.73 ppm (m, 6H), 7.68 ppm (d, 2H), 7.65-7.62 ppm (m, 4H), 7.58-7.49 ppm (m, 4H)

Methyl: 1.72 ppm (s, 6H), 1.69 ppm (s, 12H)

Example 2

Production of Organic Light-Emitting Device

The above described organic light-emitting device having the layer structure described in the first specific example was produced.

A film of indium tin oxide (ITO) was formed on a glass substrate by a sputtering method to form an anode. The film thickness of the anode was set to be 120 nm. Next, the anode was subjected to ultrasonic cleaning sequentially with acetone and isopropyl alcohol (IPA), and subsequently boiling-cleaned in IPA, and then dried. After that, the anode was cleaned with UV light/ozone. The substrate thus processed was used as a transparent electroconductive supporting substrate.

Next, a film of Compound (C) shown below was formed on the anode by a vacuum vapor-deposition method to form a hole transporting layer. The film thickness of the hole transporting layer was set to be 30 nm, the vacuum degree during the vapor deposition was set to be $1.0 \times 10^{-4}$ Pa, and the film-forming rate was set to be 0.1 nm/sec.

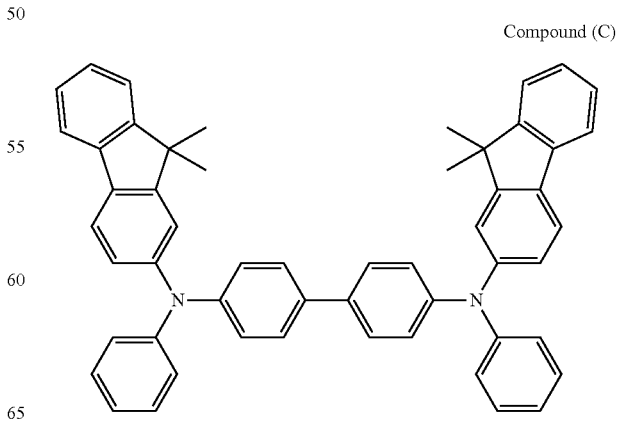

Next, a light-emitting layer was formed on the hole transporting layer by depositing together illustrative Compound C-3 as a host and Compound (D) as a guest shown below by a vacuum vapor-deposition method so that the content of Compound (D) was 3 wt % with respect to the total amount of the light-emitting layer. The film thickness of the light-emitting layer was set to be 50 nm, the vacuum degree during the vapor deposition was set to be $1.0\times10^{-4}$ Pa, and the film-forming rate was set to be 0.1 nm/sec.

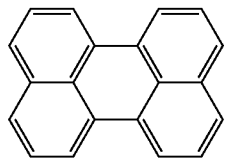

Compound (D)

Next, a film of bathophenanthroline (BPhen) was formed on the light-emitting layer by a vacuum vapor-deposition method to form an electron transporting layer. The film thickness of the electron transporting layer was set to be 40 nm, the vacuum degree during the vapor deposition was set to be $1.0\times10^{-4}$ Pa, and the film forming rate was set to be 0.2 nm/sec to 0.3 nm/sec.

Thereafter, a film of potassium fluoride was formed on the electron transporting layer by a vacuum vapor-deposition method to form a KF film. The film thickness of the KF film was set to be 0.5 nm. Then, a film of aluminum was formed on the KF film by a vacuum vapor-deposition method to form an Al film. The film thickness of the Al film was set to be 150 nm, the vacuum degree during the vapor deposition was set to be $1.0\times10^{-4}$ Pa, and the film-forming rate was set to be 1.0 nm/sec to 1.2 nm/sec. The above KF film and Al film (aluminum-potassium alloy film) function as an electron injecting electrode (cathode).

The device was covered with glass plates for protection in a dry air atmosphere and the glass plates were sealed with an acrylic adhesive so that the device did not deteriorate due to the adsorption of moisture. The organic light-emitting device was obtained as described above.

A voltage was applied to the device thus obtained so that the ITO electrode (anode) was a positive electrode and the Al electrode (cathode) was a negative electrode, and as a result, light emission was confirmed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-285377, filed Nov. 6, 2008, which is hereby incorporated by reference herein in its entirety.

The invention claimed is:

1. A dibenzo[c,g]fluorene compound having two dibenzo[c,g]fluorene skeletons, which is represented by the following general formula [1]:

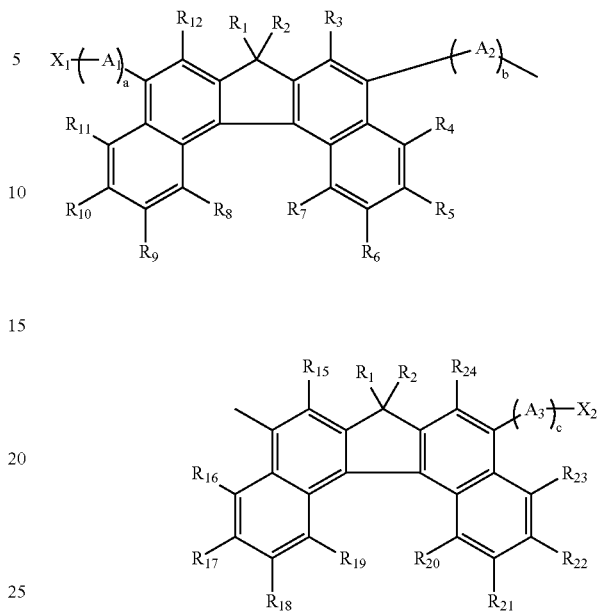

wherein $X_1$ and $X_2$ each represent a hydrogen atom, a substituted or unsubstituted aryl group, or a substituted or unsubstituted alkyl group, and may be the same or different; $A_1$ to $A_3$ each represent a substituted or unsubstituted arylene group, and may be the same or different; $R_1$ to $R_{24}$ each represent a hydrogen atom, or a substituted or unsubstituted alkyl group, and may be the same or different; a, b and c are each an integer of 0 to 4, provided that a+b+c is 0 or more and 4 or less; when a is 2 or more, $A_1$'s may be the same or different; when b is 2 or more, $A_2$'s may be the same or different; and when c is 2 or more, $A_3$'s may be the same or different.

2. The dibenzo[c,g]fluorene compound according to claim 1, wherein a and b are 0, and $X_1$ and $X_2$ are each a hydrogen atom or a substituted or unsubstituted alkyl group.

3. The dibenzo[c,g]fluorene compound according to claim 1, wherein $A_2$ is a substituent selected from the group consisting of a substituted or unsubstituted phenylene group, a substituted or unsubstituted biphenylene group, a substituted or unsubstituted terphenylene group, a substituted or unsubstituted naphthylene group, a substituted or unsubstituted anthrylene group, a substituted or unsubstituted phenanthrylene group, a substituted or unsubstituted pyrenylene group and a substituted or unsubstituted fluorenylene group.

4. An organic light-emitting device comprising an anode, a cathode and an organic compound layer sandwiched between the anode and the cathode, wherein at least one layer among the organic compound layers comprises at least one dibenzo[c,g]fluorene compound according to claim 1.

5. The organic light-emitting device according to claim 4, wherein the compound is contained in a light-emitting layer.

6. The organic light-emitting device according to claim 5, wherein the light-emitting layer comprises a host and a guest, and the host is the dibenzo[c,g]fluorene compound.

* * * * *